United States Patent
Zhang et al.

(10) Patent No.: US 10,946,038 B2
(45) Date of Patent: Mar. 16, 2021

(54) CANCER TREATMENT USING BETA-(1-3)-(1-4)-GLUCAN

(71) Applicant: Case Western Reserve University, Cleveland, OH (US)

(72) Inventors: Mei Zhang, Cleveland, OH (US); Alex Y. Huang, Cleveland, OH (US); Julian Kim, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 152 days.

(21) Appl. No.: 16/059,511

(22) Filed: Aug. 9, 2018

(65) Prior Publication Data
US 2019/0046557 A1   Feb. 14, 2019

Related U.S. Application Data

(60) Provisional application No. 62/542,958, filed on Aug. 9, 2017.

(51) Int. Cl.
| | |
|---|---|
| *A61K 35/00* | (2006.01) |
| *A61K 31/716* | (2006.01) |
| *A61P 35/00* | (2006.01) |

(52) U.S. Cl.
CPC .......... *A61K 31/716* (2013.01); *A61P 35/00* (2018.01)

(58) Field of Classification Search
CPC ................................ A61K 31/76; A61P 35/00
See application file for complete search history.

(56) References Cited

U.S. PATENT DOCUMENTS 7,507,724 B2 * 3/2009 Cheung ................ A61K 31/739
514/54

OTHER PUBLICATIONS

Zhang and Kim, Effect of molecular size and modification pattern on the internalization of water soluble Beta-(1-->3)-(1-->4)-glucan by primary murine macrophages (International Journal of Biochemistry and Cell Biology) (2012) pp. 914-927 (IDS No. 11) (Year: 2012).*
Ruella et al. Adoptive Immunotherapy for Cancer, 2013, Immunological Review p. 14-38 (Year: 2013).*
Zhang and Kim, Effect of molecular size and modification pattern on the internalization of water soluble B-glucan by primary murine macrophages, 2012, International Journal of Biochemistry and Cell Biology, p. 914-927 (Year: 2012).*
Yi, Huanfa, et al. "Targeting the immunoregulator SRA/CD204 potentiates specific dendritic cell vaccine-induced T-cell and response antitumor immunity." Cancer research 71.21 (2011): 6611-6620.
Bose, Nandita, et al. "Binding of soluble yeast ß-glucan to human neutrophils and monocytes is complement-dependent." Frontiers in immunology 4 (2013): 230.
Chan, Godfrey Chi-Fung, Wing Keung Chan, and Daniel Man-Yuen Sze. "The effects of ß-glucan on human immune and cancer cells." Journal of hematology & oncology 2.1 (2009): 25.

(Continued)

*Primary Examiner* — Renee Claytor
*Assistant Examiner* — Heather M Wolf
(74) *Attorney, Agent, or Firm* — Tarolli, Sundheim, Covell & Tummino LLP

(57) ABSTRACT

A method of treating a subject having cancer is described that includes administering a therapeutically effective amount of a β-(1,3)-(1,4) glucan to the subject. Methods of immunostimulating in a subject by administering an effective amount of a β-(1,3)-(1,4) glucan to the subject are also described.

18 Claims, 14 Drawing Sheets

(56) References Cited

OTHER PUBLICATIONS

Cheung, Nai-Kong V., and Shakeel Modak. "Oral (1-3),(1-4)-ß-d-glucan synergizes with antiganglioside GD2 monoclonal antibody 3F8 in the therapy of neuroblastoma." Clinical Cancer Research 8.5 (2002): 1217-1223.

Choromanska, Anna, et al. "Anticancer properties of low molecular weight oat beta-glucan—an in vitro study." International journal of biological macromolecules 80 (2015): 23-28.

Li, Bing, et al. "Yeast glucan particles activate murine resident macrophages to secrete proinflammatory cytokines via MyD88-and Syk kinase-dependent pathways." Clinical Immunology 124.2 (2007): 170-181.

Makkouk, Amani, and George J. Weiner. "Cancer immunotherapy and breaking immune tolerance: new approaches to an old challenge." Cancer research 75.1 (2015): 5-10.

Parzonko, Andrzej, et al. "Pro-apoptotic properties of (1, 3)(1, 4)-ß-D-glucan from *Avena sativa* on human melanoma HTB-140 cells in vitro." International journal of biological macromolecules 72 (2015): 757-763.

Qi, Chunjian, et al. "Differential pathways regulating innate and adaptive antitumor immune responses by particulate and soluble yeast-derived ß-glucans." Blood 117.25 (2011): 6825-6836.

Quezada, Sergio A., et al. "Shifting the equilibrium in cancer immunoediting: from tumor tolerance to eradication." Immunological reviews 241.1 (2011): 104-118.

Ruella, Marco, and Michael Kalos. "Adoptive immunotherapy for cancer." Immunological reviews 257.1 (2014): 14-38.

Schreiber, Robert D., Lloyd J. Old, and Mark J. Smyth. "Cancer immunoediting: integrating immunity's roles in cancer suppression and promotion." Science 331.6024 (2011): 1565-1570.

Vannucci, Luca, et al. "Immunostimulatory properties and antitumor activities of glucans." International journal of oncology 43.2 (2013): 357-364.

Vetvicka, Vaclav, Brian P. Thornton, and Gordon D. Ross. "Soluble beta-glucan polysaccharide binding to the lectin site of neutrophil or natural killer cell complement receptor type 3 (CD11b/CD18) generates a primed state of the receptor capable of mediating cytotoxicity of iC3b-opsonized target cells." The Journal of clinical investigation 98.1 (1996): 50-61.

Yan, Jun, Daniel J. Allendorf, and Brian Brandley. "Yeast whole glucan particle (WGP) ß-glucan in conjunction with antitumour monoclonal antibodies to treat cancer." Expert opinion on biological therapy 5.5 (2005): 691-702.

Yi, Huanfa, et al. "Targeting the immunoregulator SRA/CD204 potentiates specific dendritic cell vaccine-induced T-cell response and antitumor immunity." Cancer research 71.21 (2011): 6611-6620.

Zanganeh, Saeid, et al. "Iron oxide nanoparticles inhibit tumour growth by inducing pro-inflammatory macrophage polarization in tumour tissues." Nature nanotechnology 11.11 (2016): 986.

Zhang, Mei, and Julian A. Kim. "Effect of molecular size and modification pattern on the internalization of water soluble ß-(1-3)-(1-4)-glucan by primary murine macrophages." The international journal of biochemistry & cell biology 44.6 (2012): 914-927.

* cited by examiner

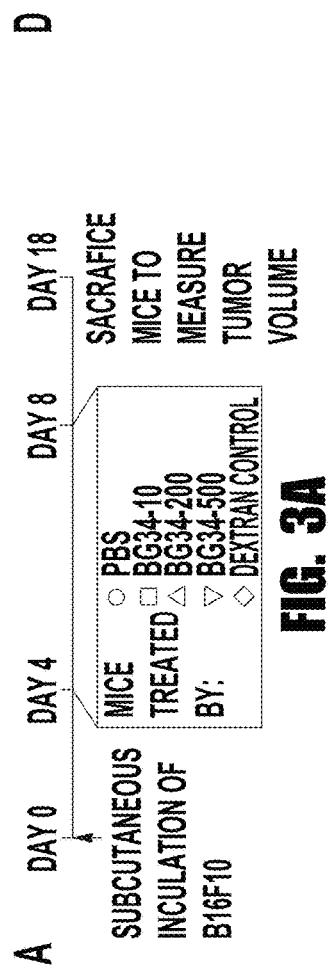

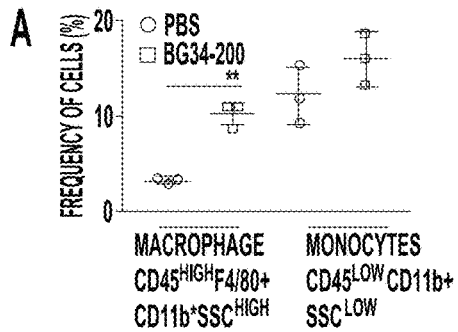
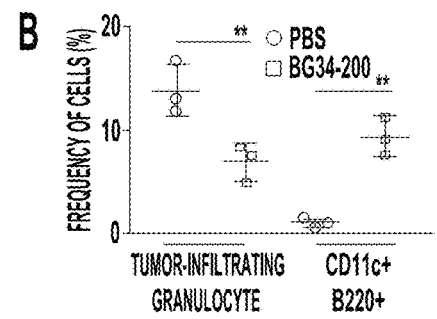
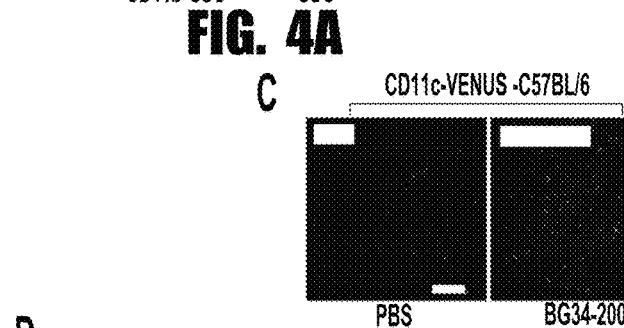
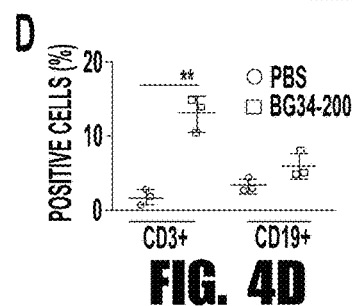
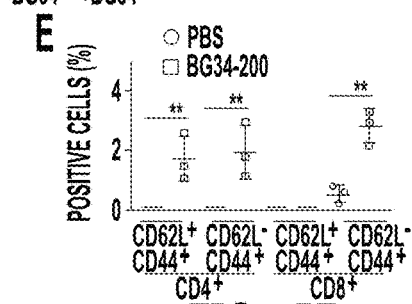
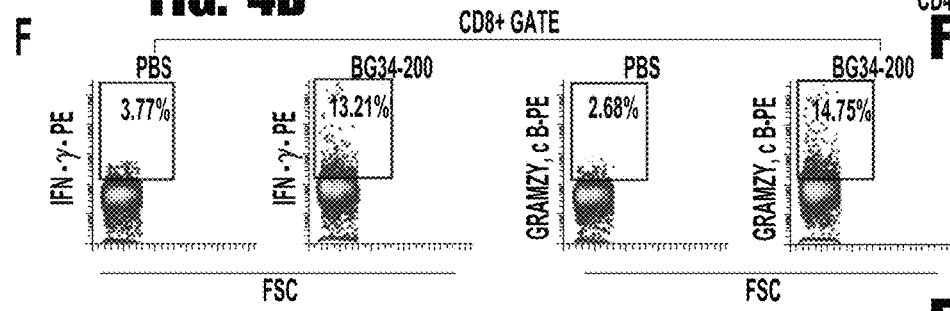
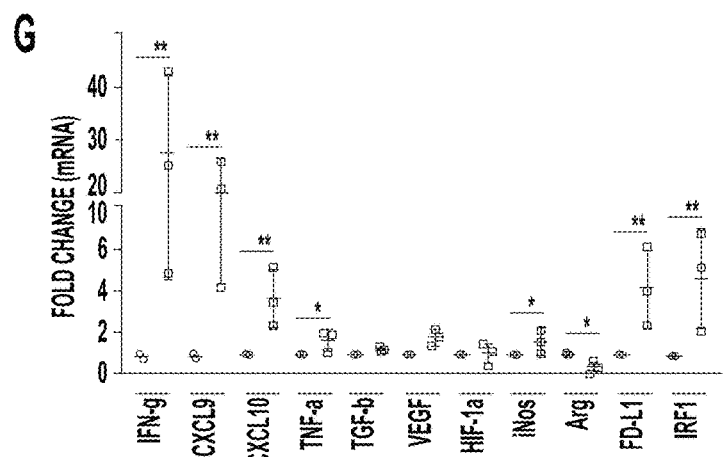

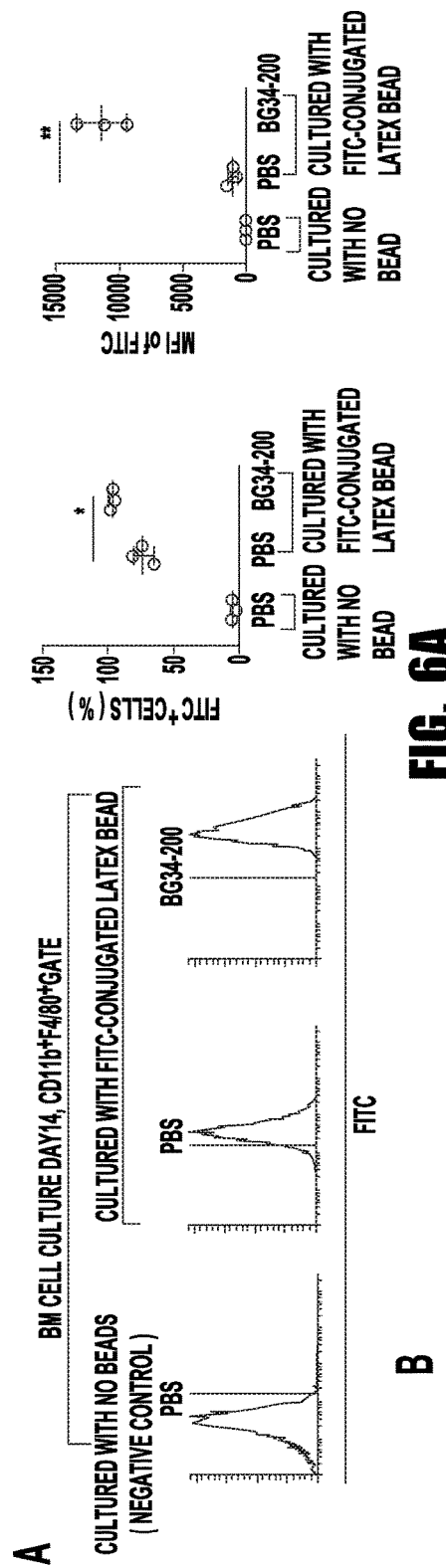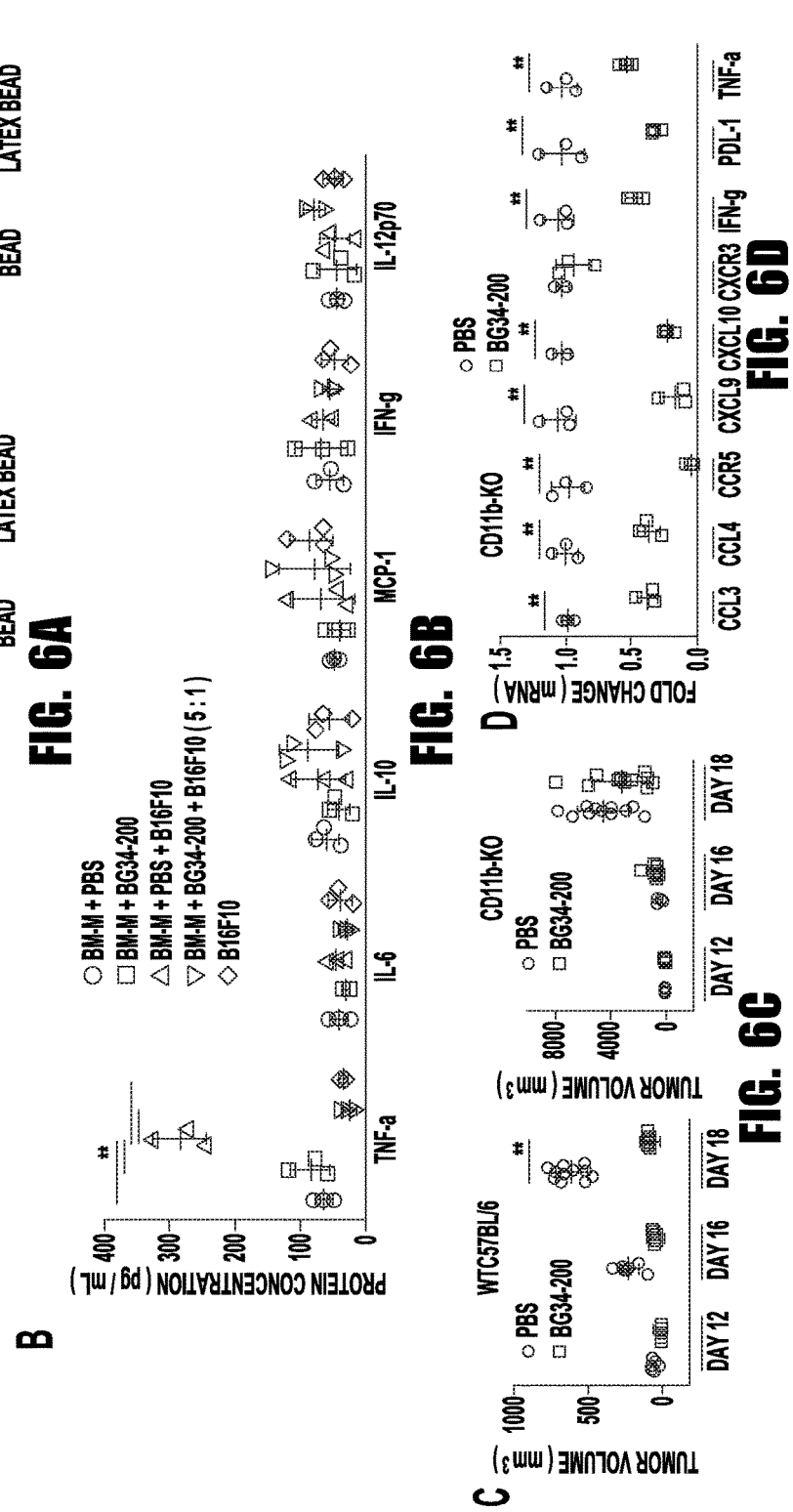
FIG. 6A
FIG. 6B
FIG. 6C
FIG. 6D

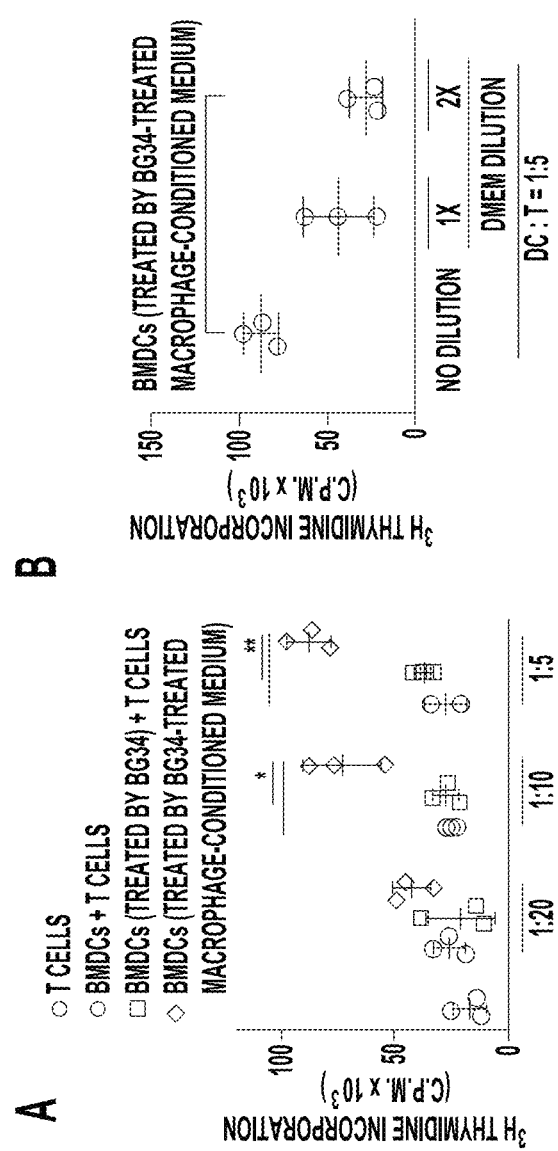
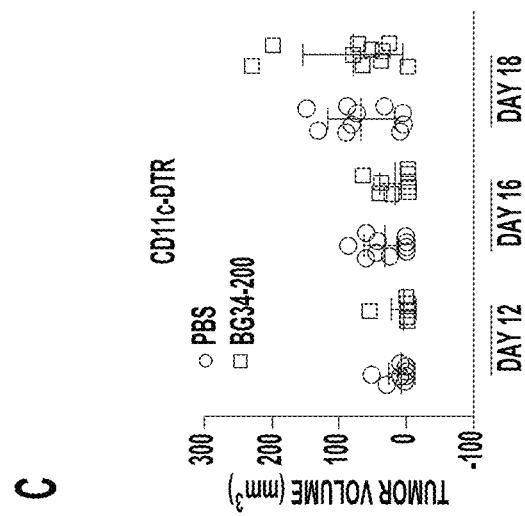
FIG. 7A
FIG. 7B
FIG. 7C

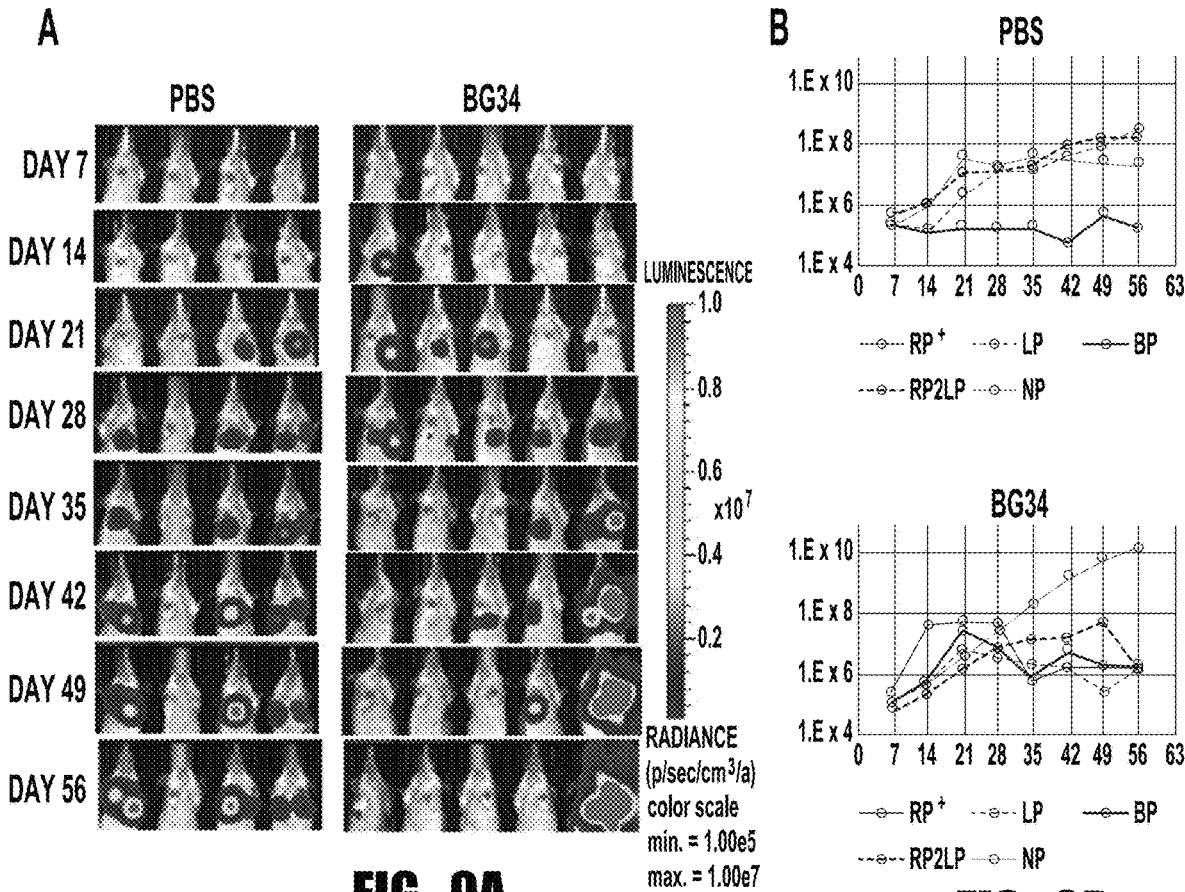
FIG. 9A
FIG. 9B
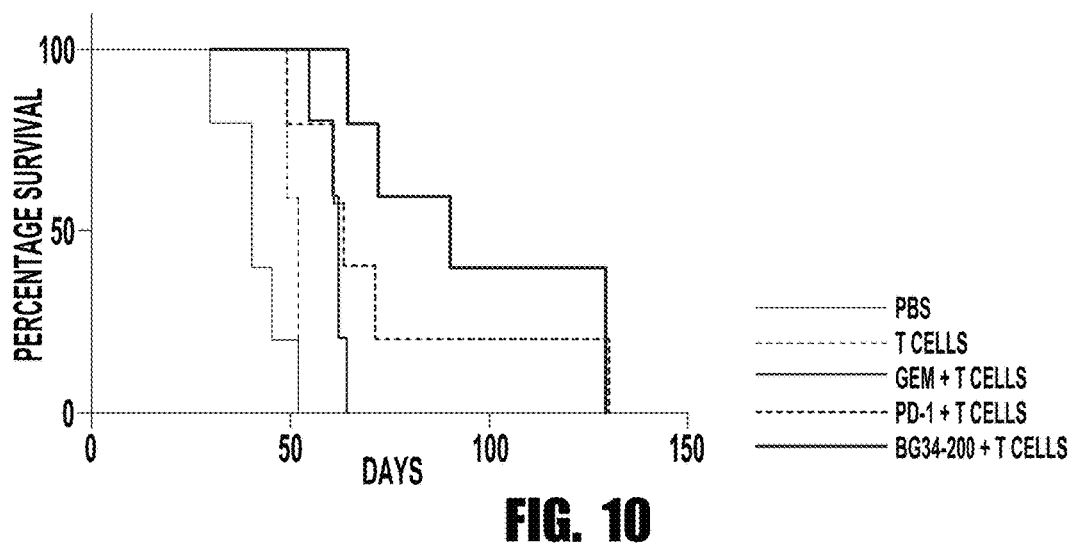
FIG. 10

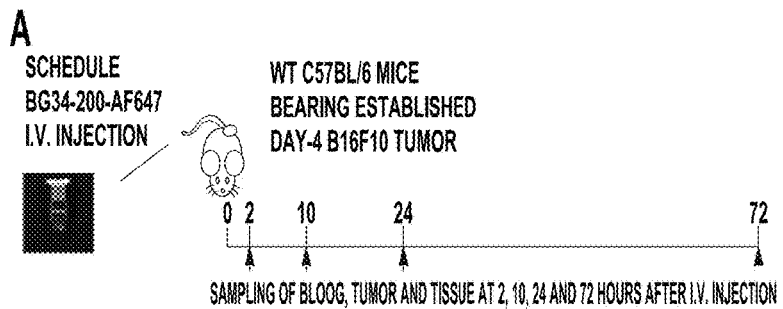
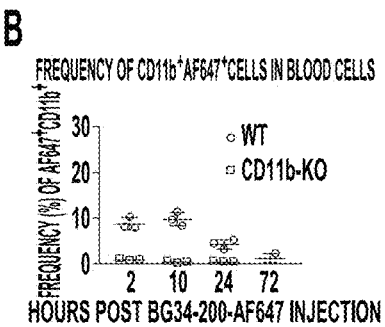
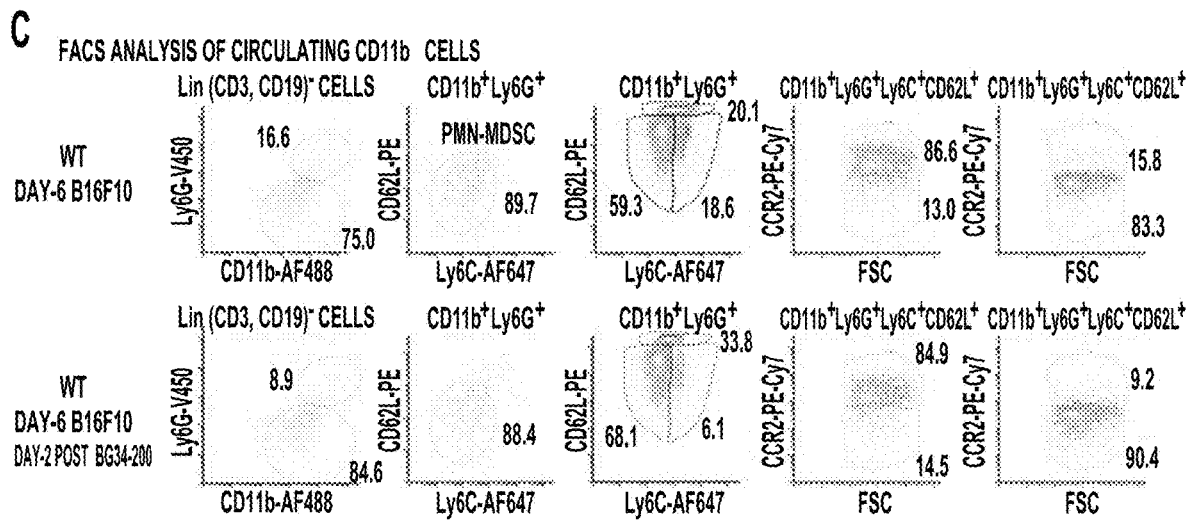
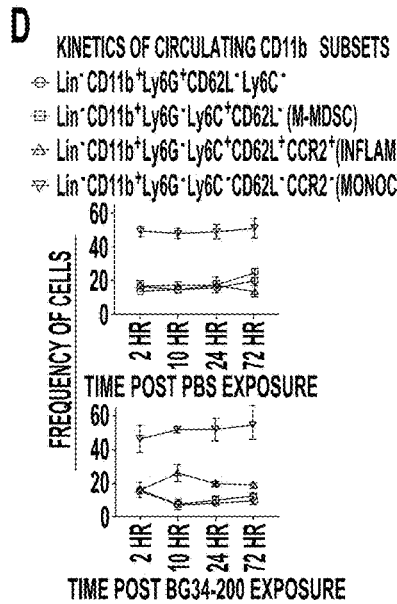
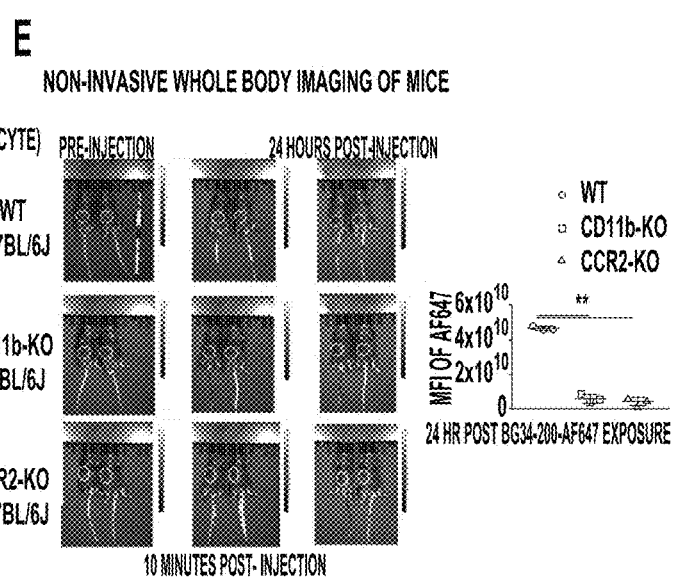

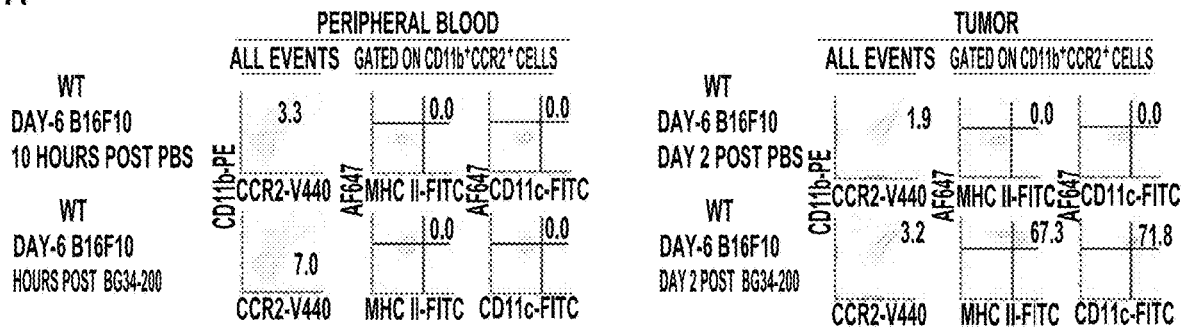
FIG. 12A
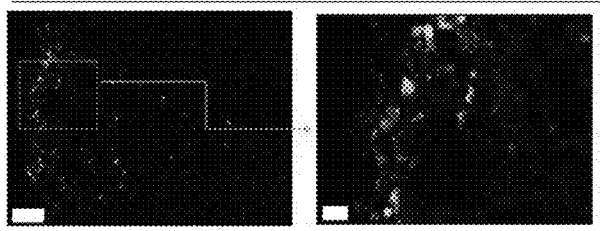
FIG. 12B
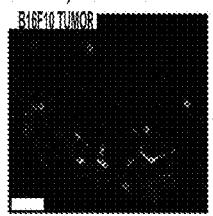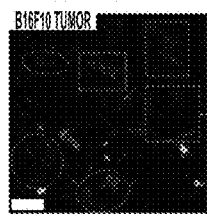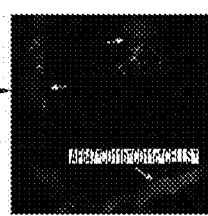
FIG. 12C

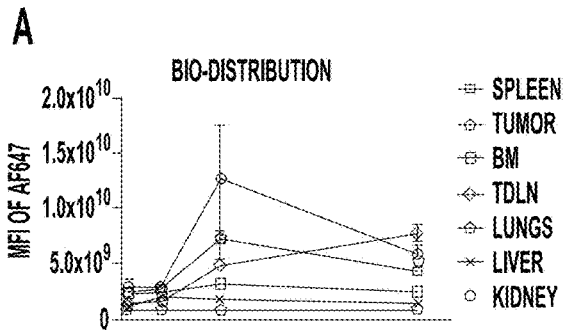
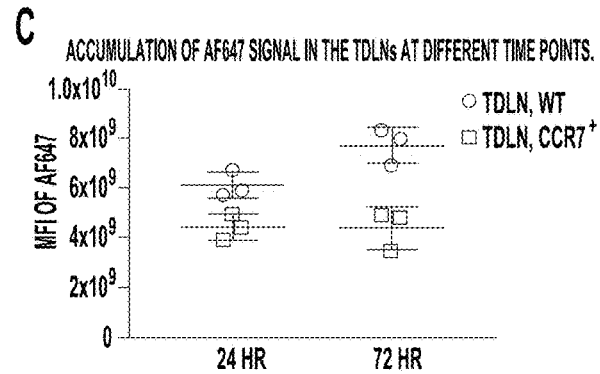
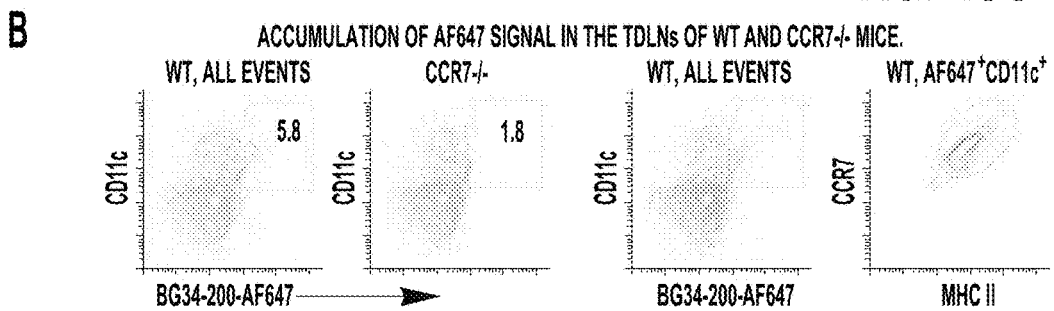
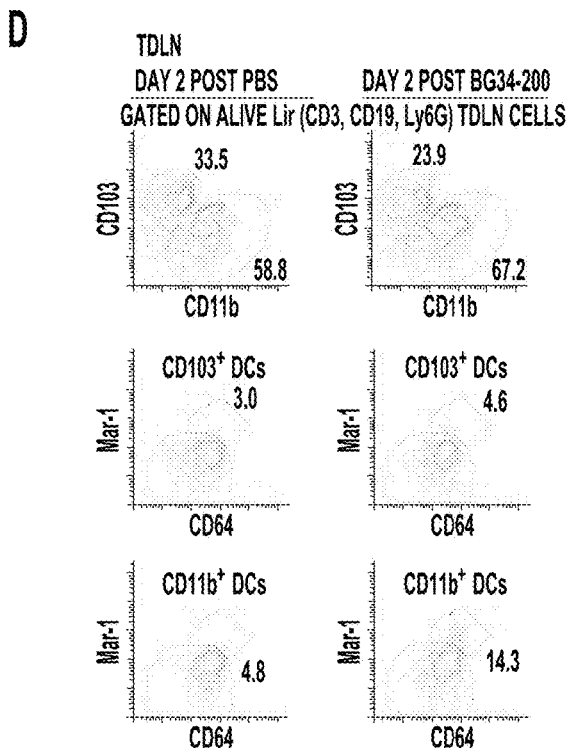
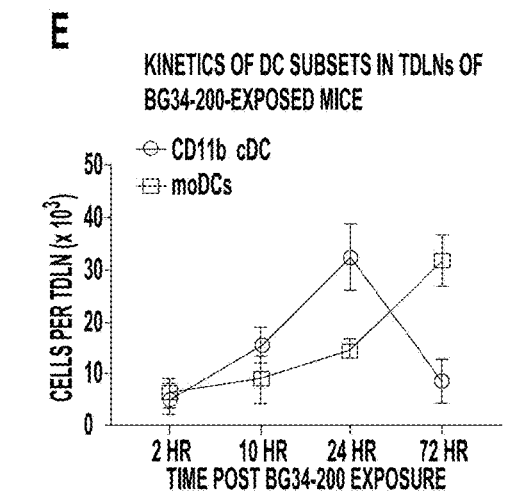

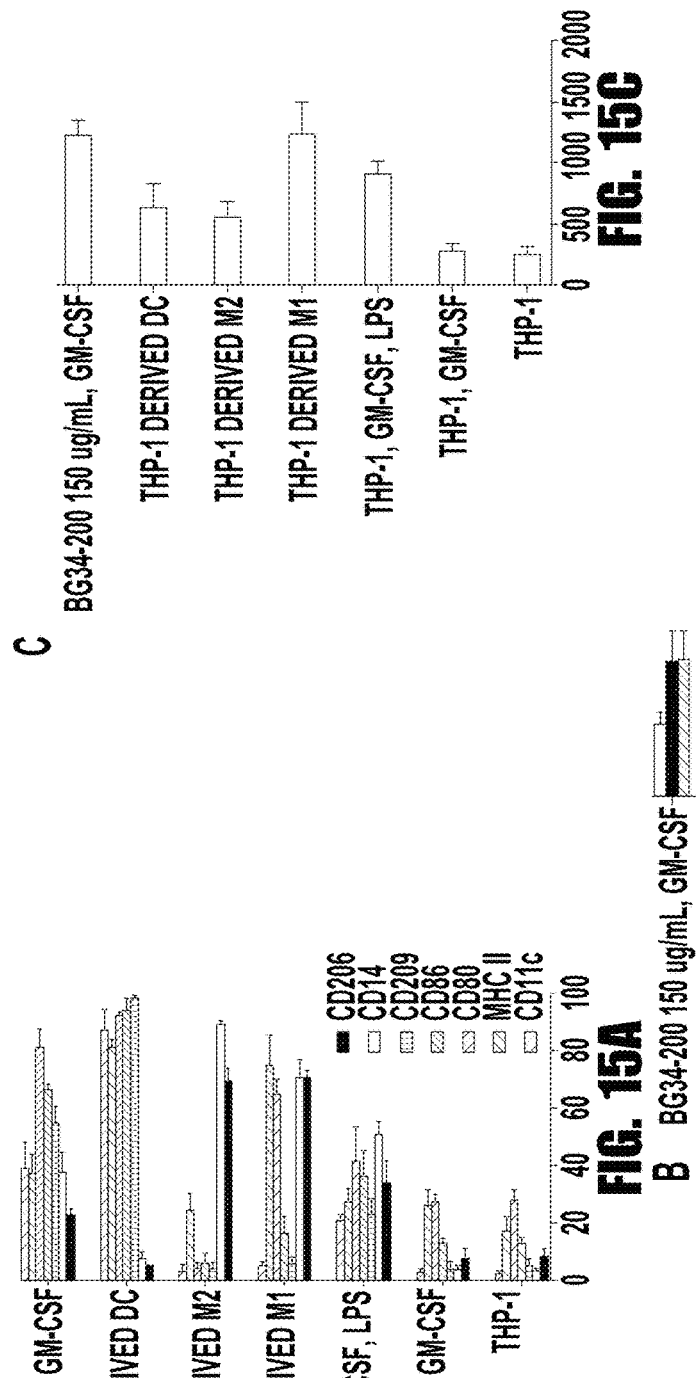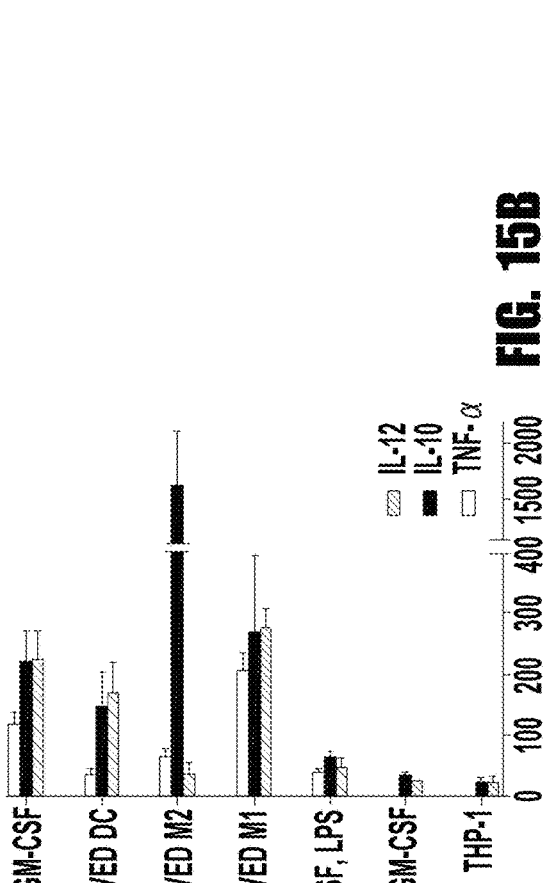

CANCER TREATMENT USING BETA-(1-3)-(1-4)-GLUCAN

CROSS-REFERENCE TO RELATED APPLICATIONS

This application claims priority to U.S. Provisional Application Ser. No. 62/542,958, filed on Aug. 9, 2017, the disclosure of which is hereby incorporated by reference in its entirety.

GOVERNMENT FUNDING

This invention was made with government support under grant numbers R21CA181875 and R21CA218790 awarded by the National Institute of Health. The Government has certain rights in the invention.

BACKGROUND

Cancer immunotherapy achieves immune-mediated control of tumor growth and metastasis by mounting tumor-reactive T cell responses. Although immunotherapy holds great promise for cancer treatment, its clinical success has so far been limited. Increasingly, studies have demonstrated that cancer cells exploit multiple mechanisms to create an immunosuppressive environment that enable them to escape immune destruction. Schreiber et al., Science, 331(6024): p. 1565-70 (2011). Therefore, overcoming immunosuppressive mechanisms and induction of durable antitumor immunity using novel immune modulators are essential goals of cancer immunotherapy.

It has previously been demonstrated that β-glucan molecules can be exploited as immune modulators for generating antitumor immune responses, which is based on their ability to integrate innate and adaptive immune components. Chan et al., J Hematol Oncol, 2: p. 25 (2009). β-glucans (or polysaccharides) are major cell wall components of microbes. Their carbohydrate structures can be recognized as pathogen associated molecular pattern (PMAP) by pattern recognition receptor (PRR) such as dectin-1 and CR3, which are C-type lectin and carbohydrate PRR. Similar to other PRR such as toll-like receptors (TLRs), carbohydrate PRRs are also involved in host defense mechanisms against infection. However, different from TLRs that recognize various PAMPs such as lipopolysaccharide, proteoglycans, DNAs and RNAs, C-type lectins appear to be more specific and mostly recognize carbohydrate structures. Because of the specific recognition, some β-glucans display a capability of stimulating host immune responses via priming macrophage, neutrophil and granulocytes through dectin-1 and/or complement receptor 3 (CR3). Yan et al., Expert Opin Biol Ther, 5(5): p. 691-702 (2005). β-glucan mediated action on these receptors can further trigger natural killer (NK) cells, dendritic cells (DCs) and T cells to respond to tumor targets. Vetvicka et al., J Clin Invest, 98(1): p. 50-61 (1996). The glucan molecule-mediated immunomodulation has been attributed to its efficient modulatory function during pathogen recognition and antigen presentation. More importantly, studies on soluble β-glucan have demonstrated that the β-glucan-bound monocytes and neutrophils can mediate direct binding of these cells to complement 3 opsonized targets such as iC3b-bound tumor cells, which provides a cellular mechanism of β-glucan to target tumor environment. Bose et al., Front Immunol, 4: p. 230 (2013). Therefore, modification of tumor environment using novel glucan-type immune modulator can potentially enhance immunogenicity of tumor.

The mechanism of β-(1-3)-(1-6)-glucan in inducing pro-inflammatory cytokine secretion and stimulating innate and adaptive immune responses has been investigated (Liu et al., J Immunol, 195(10): p. 5055-65 (2015)), and multiple clinical trials of cancer immunotherapy have incorporated β-(1-3)-(1-6)-glucan in therapeutic antibody treatment against cancer. Glucan-induced direct manipulation of antibody sensitized tumor microenvironment has also been reported to elicit a potent antitumor response. Vannucci et al., Int J Oncol, 43(2): p. 357-64 (2013). β-glucans can be obtained from a wide variety of sources, including cereals, fungi, seaweed, yeast, and bacteria. Chan et al., J. Hematol. Oncol. 2:25. doi: 10.1186/1756-8722-2-25. However, emerging data suggest that β-glucans from different resources with different impurities, glycosidic linkage, molecular weight, solubility, and route of administration all exhibit different mechanism of actions and potency of antitumor effect. Qi et al., Blood, 117(25): p. 6825-36 (2011); Li et al., Clin Immunol, 124(2): p. 170-81 (2007). A current limitation in studies involving β-glucan includes a lack of β-glucan control standard with specific molecular weight and branches available. Most of the β-glucans studies to-date used zymosan, which is a mixture of chitosan, β-glucans and cell wall particles; and the exact immunological actions and signaling pathway induced by β-glucan are still unclear and have to be further defined.

There is a need for natural anticancer compounds having low toxicity to normal cells. The inventors have previously engineered oat-derived β-(1-3)-(1-4)-glucans (BG34) with well-characterized molecular weight and chemical structure. Zhang, M., Kim, J. A., J Biochem Cell Biol, 44(6): p. 914-27 (2012). These glucan samples adopt linear chain structure with no branches. They are highly purified glucan with carbohydrate content over 98% and have been documented to be free of endotoxin. Since studies have demonstrated that the peptide/protein impurities, endotoxin contaminants and broad molecular weight distribution could significantly affect β-glucan-mediated activity, these unique features of BG34 make them excellent candidates for pre-clinical/clinical studies and necessary approval by regulatory agencies.

SUMMARY

Converting an immunosuppressive melanoma microenvironment into one that favors the induction of antitumor immunity is important for effective cancer immunotherapy. The inventors demonstrate herein that oat-derived β-(1-3)-(1-4)-glucan of 200 kDa molecular size (BG34-200), which was previously shown to mediate direct interaction with macrophages, could alter the immune signature within melanoma microenvironment. Systemic administration of BG34-200 resulted in reversion of tolerant melanoma microenvironment to an immunogenic one that allows M1-type activation of macrophages, the induction of pro-inflammatory cytokines/chemokines including IFN-γ, TNF-α, CXCL9, and CXCL10, and enhanced IRF1 and PD-L1 expression. In turn, BG34-200 induced a superior antitumor response against primary and lung metastatic B16F10 melanoma compared to untreated controls. The enhanced tumor destruction was accompanied with significantly increased tumor infiltration of $CD4^+$ and $CD8^+$ T cells as well as elevated IFN-γ in the tumor sites. Systemic administration of BG34-200 also provoked systemic activation of tumor draining lymph node T cells that recognize antigens naturally expressing in melanoma (gp100/PMEL). Mechanistic studies using CD11b-knockout (KO), CD11c-DTR transgenic mice and nude mice revealed that macrophages, DCs, T cells were all required for the BG34-200-induced therapeutic benefit. Studies using IFN-γ-KO transgenic mice showed that IFN-γ was essential for the BG34-200-elicited antitumor response. Beyond melanoma, the therapeutic efficacy of BG34-200 and its immune stimulating activity were demonstrated in a mouse model of osteosarcoma. Treatment of pancreatic cancer using BG34-200 and adoptive immunotherapy was also demonstrated. The results shown that BG34-200 is highly effective in modulating antitumor immunity, and support its use in the treatment of cancer such as metastatic melanoma.

Further, the inventors demonstrate that the systemic administration of BG34-200 resulted in significant increase of circulating inflammatory monocytes that gave rise to DCs in tumor sites and tumor draining lymph nodes (TDLN). This associated with T-cell activation and resulted in striking regression of melanoma, osteosarcoma and pancreatic tumor. This also resulted in a protective response to secondary tumor challenge in mice. Mechanistic studies using human monocyte THP-1 cell line revealed that the BG34-200 exposure could promote the monocyte differentiation into dendritic cells (DCs) with significantly upregulated activation markers (CD80, CD86, MHC II and CD11c), increased production of inflammatory cytokine (TNF-α and IL-12) and enhanced phagocytosis. These results revealed the BG34-modulation of monocytes (innate immunity) for memorable antitumor immune responses (trained antitumor immunity). More importantly, using the THP-1 cell model, the inventors generated bioanalytical data revealing that the bioactivity of BG34 molecules are significantly affected by Mw. The BG34 molecules in the range 100 Kda-300 Kda can most effectively promote the monocyte differentiation into DCs, thus mediate robust innate and adaptive immune responses against tumor.

BRIEF DESCRIPTION OF THE FIGURES

The present invention may be more readily understood by reference to the following drawings, wherein:

FIGS. 3A-G provides graphs and images showing that systemic administration of BG34-200 induces a potent anti-melanoma response. (A) Schedule for subcutaneous inoculation of B16F10. WT C57BL/6 mice inoculated with subcutaneously injected B16F10 and treated by PBS, BG34-10, BG34-200, BG34-500 and dextran. (B) Tumor volumes in WT C57BL/6 mice bearing established B16F10 and different treatments. Tumor volumes at preclinical endpoint (day 18) for individual animals in each group were graphed. n=10 per group. p<0.01. Significance was determined by two-way ANOVA with Student's t test. (C) Photographs of tumors of representative mouse of untreated (PBS) and BG34-200 treatment. (D) Survival of mice treated by PBS or BG34-200. (n=10 per group). (E) Schedule for i.v. inoculation of B16F10. WT C57BL/6 mice inoculated with i.v. injected B16F10 and treated by PBS and BG34-200. (F) Photographs of lungs of representative mouse of untreated (PBS) and BG34-200-treated. (G) The number of metastatic nodules in lungs of untreated (PBS) and BG34-200-treated mouse. n=8 per group. p<0.01. Significance was determined by two-way ANOVA with Student's t test.

FIGS. 4A-G provides graphs showing BG34-200 treatment promotes immune activation in the tumor site. The WT C57BJ/6 mice were inoculated with subcutaneously injected B16F10 and treated by PBS or BG34200. Three days after treatment, tumors from PBS- and BG34-200 treated mice were harvested for FACS analysis and qPCR. (A) The frequency of tumor-infiltrating macrophage and monocytes by FACS. (B) The frequency of tumor-infiltrating granulocytes and DCs by FACS. (C) Fluorescence microscopic imaging of B16F10 tumor tissues from CD11c-venus C57BL/6 mice treated by PBS or BG34-200 (Left). Fluorescence intensity of tumors treated without BG34-200 (−BG34) and with BG34-200 (+BG34-200) (Right). Data were graphed as means±SD. Each data point represents fluorescence intensity of one region of interest. (D) The frequency of tumor infiltrating T (CD3$^+$) and B (CD19$^+$) cells by FACS. (E) The frequency of tumor-infiltrating CD62L$^+$CD44$^+$ and CD62L$^-$CD44$^+$ cells in CD4$^+$ and CD8$^+$ populations by FACS. (F) The intracellular frequency of IFN-γ and Granzyme B by CD8$^+$ populations within tumors. (G) RNA expression in B16F10 tumor tissues from WT C57BL/6 mice treated by PBS or BG34-200. For (A), (B), (D), (E), (F) and (G), n=9 per group. (A), (B), (D), (E) and (G) data were graphed as means±SD. For (A), (B), (D) and (E), each data point represents pooled samples from three mice. For (G), each data point represents one of three replicates of RNA samples from individual tumor. *p<0.05, **p<0.01. Significance was determined by two-way ANOVA with Student's t test.

FIGS. 6A-D provides graphs showing CD11b+ cells are required for BG34-200-induced anti-melanoma responses. (A) Bone marrow derived macrophages (BM-Ms) were cultured with BG34-200 in the presence of M CSF for 14 days. PBS-treated BM-Ms served as treatment control. The PBS- or BG34-200-treated BM-Ms were then co-cultured with FITC-conjugated latex beads to determine phagocytic activity. PBS-treated BM-Ms with no beads serve as control. Left: FACS histograms showing the frequencies of FITC cells in the CD11b$^+$F4/80$^+$-gated BM-M cell populations. Middle: Percentage of FITC cells in CD11b$^+$F4/80$^+$BM-Ms. Right: Mean fluorescence intensity (MFI) of FITC cells in CD11b$^+$F4/80$^+$-BM-Ms. (B) Inflammatory cytokine concentration in cell conditioned media. BM-Ms were cultured with BG34-200. PBS-treated BM-Ms served as control. The PBS- and BG34-200-treated BM-Ms were then co-cultured with B16F10 tumor cells at BM-M to B16F10 ratio 5:1. BM-M or B16F10 cell conditioned media served as controls Inflammatory cytokines (TNF-α, IL-6, IL-10, MCP-1, IFN-γ and IL-12p70) in cell conditioned media were determined by cytometric bead array. For (A) and (B), data were graphed as means±SD. Each data point represents one of three replicates of samples from individual BM-M cultures. (C) Tumor volumes in WT C57BJ/6 or CD11b-KO mice bearing established B16F10 with or without BG34 200 treatment. Tumor volumes at day 12, 16 and 18 for individual animals in each group were graphed. n=9 per group. (D) RNA expression in B16F10 tumor tissues from CD11b-KO mice treated by PBS or BG34-200. Each data point represents one of three replicates of RNA samples from individual tumor. For (A)-(D), *p<0.05, **p<0.01. Significance was determined by two-way ANOVA with Student's t test.

FIGS. 7A-C provides graphs showing CD11c$^+$ cells are required for BG34-200-induced anti-melanoma responses. (A) 3H thymidine assay of PMEL CD8$^+$ T cells co-cultured with gp100$_{25-33}$ peptide-pulsed BMDCs. T cells alone served as negative control. BMDCs were treated by PBS or BG34-200, or BG34-200 treated macrophage-conditioned medium. BMDCs pulsed with gp100$_{25-33}$ peptide and co-cultured with PMEL CD8$^+$ T cells at DC:T ratios of 1:20, 1:10 and 1:5. (B) BG34-200-treated macrophage-conditioned medium at three different dilutions with DMEM were used to co-culture with BMDCs. Then BMDCs were pulsed with gp100$_{25-33}$ peptide and co-cultured with PMEL CD8$^+$ T cells at DC:T ratios of 1:5. (C) Tumor volumes in CD11c-KO mice bearing established B16F10 with or without BG34-200 treatment. Tumor volumes at day 12, 16 and 18 for individual animals in each group were graphed. n=9 per group. *p<0.05, **p<0.01. Significance was determined by two-way ANOVA with Student's t test.

FIGS. 9A-B provides graphs and images showing systemic administration of BG34-200 induces antitumor responses in K7M2-Luc2 osteosarcoma model of Balb/c mice. Balb/c mice bearing i.v. injected K7M2-Luc2 osteosarcoma cells were administered with BG34-200 intranasal once a week for 7 weeks. PBS-treated mice bearing i.v. injected K7M2-Luc2 osteosarcoma cells served as control. Tumor volume were quantified by non-invasive imaging of luciferase signal. (A) Weekly whole body imaging of mice treated by PBS or BG34-200. (B) Mean fluorescence intensity of PBS-treated (up) and BG34-200 treated (down) mice at various time points. For PBS group, n=4; for BG34-200 group, n=5.

FIG. 10 provides a graph showing the effect of treatment on the survival of mice bearing pancreatic tumor (AsPC-1). Phosphate buffer saline (PBS) treated mice served as a control. The treatment groups included T cells, T cells+gemcitabine, T cells+PD-1, and T cells+BG34-200. Mice treated with T cells+BG34-200 showed the highest percentage survival over time.

FIGS. 11A-E provides graphs and images showing that circulating inflammatory monocytes (CD11b$^+$CCR2$^+$) significantly increased upon BG34-200 administration and drove the tumor accumulation of BG34-200-AF647. (A) Treatment schedule of AF647-tagged BG34-200. (B) The Lin(CD3, CD19)$^+$ cells were gated out because these cells were found not to interact with fluorescent BG34-200 (data not shown). The Lin(CD3, CD19)$^-$ cells were then gated for AF647 and CD11b, showing that almost all the circulating cells that have bound with or taken up fluorescent BG34-200 were CD11b$^+$ cells (Data not shown). Then the frequency of circulating CD11b$^+$AF647$^+$ cells in the blood samples of WT and CD11b-KO mice upon BG34-200-AF647 treatment were analyzed by FACS, showing that the AF647 signals were significantly decreased in circulating leukocytes of CD11b-KO mice. (C) The circulating CD11b$^+$ cells in the context of melanoma can be separated into granulocytic MDSC (Lin$^-$CD11b$^+$Ly6G$^+$CD62L$^-$Ly6C$^-$), monocytic MDSC (Lin$^-$CD11b$^+$Ly6G$^-$Ly6C$^+$CD62L$^-$), inflammatory monocyte (Lin$^-$CD11b$^+$Ly6G$^-$Ly6C$^+$CD62L$^+$CCR2$^+$), and resident monocyte (Lin$^-$CD11b$^+$Ly6G$^-$Ly6C$^-$CD62L$^-$CCR2$^-$). (D) Kinetics of circulating CD11b$^+$ cell subsets upon BG34-200 treatment. BG34-200 exposure of mice bearing B16F10 tumor resulted in an increased frequency of inflammatory monocytes, and decreased frequency of M-MDSC and G-MDSC. (E) Non-invasive imaging of tumor-bearing mice receiving PBS or BG34-200. The accumulation of BG34-200-AF647 in B16F10 tumors are CD11b and CCR2 dependent. Data were graphed as mean±SD. Each data point represents pooled samples from three mice. FACS graphs represent one of three replicates of cell samples from pooled blood. **, p<0.01. Significance was determined by two-way ANOVA with student's t-test.

FIG. 12A-D provides graphs and images showing that the circulating CD11b$^+$CCR2$^+$ cell subset gives rise to CD11b$^+$CD11c$^+$ dendritic cells in tumor site upon BG34-200 treatment. (A) FACS analysis of MHC II and CD11c expression by the CD11b$^+$CCR2$^+$AF647$^+$ cells in blood and tumor cell suspension of mice receiving PBS or BG34-200-AF647. These results demonstrated that the CD11b$^+$CCR2$^+$AF647$^+$ cells infiltrated to tumor where they upregulated expression of MHC II and CD11c. (C and D) Confocal fluorescence imaging of fixed tumor tissue slides of CD11c-Venus transgenic mice receiving PBS or BG34-200-AF647. The BG34-200-AF647 infiltrated to tumor environment where there was an accumulation of CD11c$^+$ cells (C), and a majority proportion of CD11b$^+$AF647$^+$ cells were found to be positive for CD11c (D). Data were graphed as mean±SD. Each data point represents fluorescence intensity of a region of interest. FACS graphs represent one of three replicates of cell samples from pooled blood or tumor cell suspensions. **, p<0.01. Significance was determined by two-way ANOVA with student's t-test.

FIGS. 13A-E provides graphs showing the BG34-200-AF647 uptake and transport to tumor-draining lymph node (TDLN) by CD11b$^+$CD11c$^+$ dendritic cells. (A) Bio-distribution of BG34-200-AF647 demonstrated that most of the fluorescent BG34-200 was taken up by lungs, tumor and spleen at 24 hours after a single intravenous administration. (B) FACS analysis of BG34-200-AF647$^+$ cells in TDLNs of WT and CCR7$^{-/-}$ mice. Most of the BG34-200-AF647 signals were found in CD11c$^+$ cells that were MHC II$^+$CCR7$^+$. Accumulation of BG34-200-AF647 in TDLN is CCR7 dependent. (C) Accumulation of BG34-200-AF647 signals in the TDLNs of WT and CCR7-/- mice at 24 and 72 hours after i.v. administration. The transport of fluorescent BG34-200 molecules to the TDLN occurred through active cellular transport and not via passive lymphatic drainage as indicated by the fact that all accumulation of fluorescent BG34-200 in the TDLNs was significantly decreased in CCR7-/- mice. (D) FACS analysis of DC subsets in TDLNs of mice receiving PBS or BG34-200. Results indicated that the BG34-200 exposure of WT mice bearing B16F10 resulted in increased frequency of CD11b$^+$ cDC (CD11c$^+$CD11b$^+$CCR7$^+$CD103$^-$MAR-1$^-$CD64$^-$) and mo-DCs (CD11c$^+$CD11b$^+$CCR7$^+$CD103$^-$MAR-1$^+$CD64$^+$) in TDLNs. (E) Kinetics of DC subsets in TDLNs of BG34-200-exposed mice. (A), (C) and (E), data were graphed as mean±SD. FACS graphs represent one of three replicates of cell samples.

FIGS. 15A-C provides graphs showing that the BG34-200 treatment of human monocyte THP-1 cells resulted in (A) the upregulated surface expression of CD11c, CD80, CD86, CD209 and MHC II, (B) increased production of intracellular IL12 and TNF-α, and (C) enhanced phagocytosis of fluorescent latex beads. The THP-1 cell, THP-1 cells in the presence of physiological concentration of GM-CSF, THP-1 cells in the presence of physiological concentration of GM-CSF and LPS, as well as THP-1 cell-polarized M1, M2 and DC served as control. Data are graphed as mean±SD.

DETAILED DESCRIPTION

As used herein, the terms "treatment," "treating," and the like, refer to obtaining a desired pharmacologic or physiologic effect. The effect may be therapeutic in terms of a partial or complete cure for a disease or an adverse effect attributable to the disease. "Treatment," as used herein, covers any treatment of a disease in a mammal, particularly in a human, and can include inhibiting the disease or condition, i.e., arresting its development; and relieving the disease, i.e., causing regression of the disease.

The terms "therapeutically effective" and "pharmacologically effective" are intended to qualify the amount of an agent which will achieve the goal of improvement in disease severity and the frequency of incidence over treatment of each agent by itself, while avoiding adverse side effects typically associated with alternative therapies. The effectiveness of treatment may be measured by evaluating a reduction in tumor load or decrease in tumor growth in a subject in response to the administration of anticancer agents. The reduction in tumor load may be represent a direct decrease in mass, or it may be measured in terms of tumor growth delay, which is calculated by subtracting the average time for control tumors to grow over to a certain volume from the time required for treated tumors to grow to the same volume.

As used herein, the term "tumor" refers to any neoplastic growth, proliferation or cell mass whether benign or malignant (cancerous), whether a primary site lesion or metastases.

"Pharmaceutically acceptable" as used herein means that the compound or composition is suitable for administration to a subject to achieve the treatments described herein, without unduly deleterious side effects in light of the severity of the disease and necessity of the treatment.

As used herein, a subject is a mammal, including for example livestock (including cattle, horses, pigs, chickens and sheep), and humans. In some aspects of the present invention the mammal is a companion animal (including pets), such as a dog or a cat for instance. In some aspects of the present invention, the subject may suitably be a human.

Unless defined otherwise, all technical and scientific terms used herein have the same meaning as commonly understood by one of ordinary skill in the art to which this invention belongs.

Cancer Treatment Using β-Glucan

Figure 1:
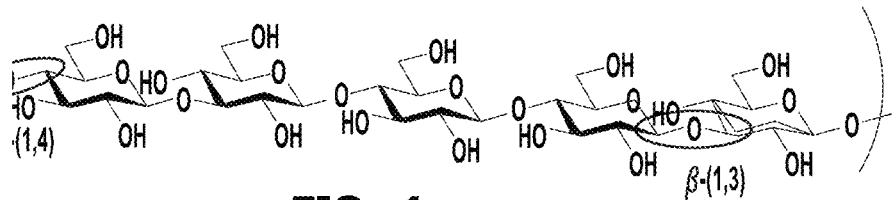
FIG. 1 provides an image showing the chemical structure of β-(1,3)-(1,4) glucan.

In one aspect, the present invention provides a method of treating a subject having cancer, comprising administering a therapeutically effective amount of a β-(1,3)-(1,4) glucan to the subject. In some embodiments, the β-(1,3)-(1,4) glucan is administered together with a pharmaceutically acceptable carrier. In further embodiments, the subject is human, while in other embodiments, the subject is a companion animal.

β-glucans are glucose polysaccharides derived from a variety of microbiological and plant sources including, for example, yeast, bacteria, algae, seaweed, mushroom, oats, and barley. β-1,3-D glucans are chains of D-glucose molecules, with the six-sided D-glucose rings connected at the 1 and 3 positions. However, there are several different types of beta glucans, which vary in backbone composition, branching, type of monomers or substituents, resulting in polysaccharides that have very different physical and biological properties (Metz, Ebert, and Weicher, Chromatographia 4:345, 1970; Manners et al. In addition, smaller side chains can branch off the 1,3 polysaccharide "backbone." For example, some β 1,3-D glucans (referred to as "β-(1,3)-(1,4) D-glucans") contain 1,4 side-chains branching off from the longer β-1,3 glucan backbone. Most β-glucans consist of β(1-3)-linked backbones with β(1-6)-linked side chains of various length and distribution, referred to as β-(1,3)-(1,6) glucans. However, β-glucan obtained from cereals such as oat or barley or wheat consists mainly of β-(1-4) bonds, and is referred to as β-(1,3)-(1-4) glucan. The chemical structure of β-(1,3)-(1-4) glucan is shown in FIG. 1. The mechanism through which β-glucans exert their immunomodulatory effects can be influenced by the structural differences between different forms of the β-glucans such as, for example, its particulate or soluble nature, tertiary conformation, length of the main chain, length of the side chain, and frequency of the side chains.

Any suitable β-(1,3)-(1,4) glucan or any combination of two or more β-(1,3)-(1,4) glucans can be administered to a subject to provide cancer treatment. Suitable β-glucans and the preparation of suitable β-glucans from their natural sources have been described by the inventors. Zhang, M., Kim, J. A., J Biochem Cell Biol, 44(6): p. 914-27 (2012). In some embodiments, the β-(1,3)-(1,4) glucan is oat-derived, meaning that oats are used as the source for the β-(1,3)-(1,4) glucan. Oat-derived β-(1,3)-(1,4) glucans purified by the inventors have a linear chain structure with no branches. Accordingly, in some embodiments, the β-(1,3)-(1,4) glucan administered to the subject a linear chain structure. The β-(1,3)-(1,4) glucan is typically highly purified, with carbohydrate content over 98%, and is free of endotoxin. The inventors have determined that β-(1,3)-(1,4) glucan having a medium molecular weight exhibits the best activity. Medium molecular weight, in this context, refers to β-(1,3)-(1,4) glucan having a weight from 50 to 500 kDa. In some embodiments, the β-(1,3)-(1,4) glucan has a molecular weight from 75 to 400 kDa. In further embodiments, the β-(1,3)-(1,4) glucan has a molecular weight from 100 to 300 kDa. In additional embodiments, the β-(1,3)-(1,4) glucan has a molecular weight from 150 to 250 kDa. In yet further embodiments, the β-(1,3)-(1,4) glucan has a molecular weight from 175 to 225 kDa, while in further embodiments, the β-(1,3)-(1,4) glucan has a molecular weight from 190 to 210 kDa.

In some embodiments, β-glucans for use in the methods of the invention include structural modifications, e.g., structural modifications not present in native glucan preparations. Such modifications may comprise, e.g., O-acetylation, methylation, alkylation, alkoylation, sulfation, phosphorylation, lipid conjugation or other modifications, as are known to one skilled in the art. In some embodiments the modification comprises modification (e.g., esterification) with an acid such as formic, succinic, citric acid, or other acid known in the art.

In some embodiments, lipid conjugation to any or all free hydroxyl groups may be accomplished by any number of means known in the art, for example, as described in Drouillat et al., Pharm. Sci. 87(1):25-30 (1998), Mbadugha et al., Org. Lett. 5 (22), 4041-4044 (2003).

In some embodiments, methylation may be accomplished and verified by any number of means known in the art, for example, as described in Mischnick et al. Carbohydr. Res. 264, 293-304 (1994); Bowie et al., Carbohydr. Res. 125, 301-307 (1984); Carpita and Shea, Linkage structure of carbohydrates by gas chromatography-mass spectrometry (GC-MS) of partially methylated alditol acetates. In Analysis of Carbohydrates by GLC and MS (Biermann, C J. & McGinnis, G. D., eds), pp. 157-216. CRC Press, Boca Raton, Fla. (1989).

In some embodiments, phosphorylation, optionally including the introduction of other modifications, and verification of the obtained product may be accomplished by means well known to those skilled in the art, see for example, Brown, Biochem. Biophys. Acta 7, 487 (1951); Roseman and Daffner, Anal. Chem. 28, 1743 (1956); Romberg and Horecker in Methods in enzymology, Vol. I, Academic Press, New York p. 323 (1955); and U.S. Pat. No. 4,818,752.

The invention provides a method of treating cancer in a subject in need thereof by administering a therapeutically effective amount of the β-glucans described herein. The term "cancer" refers to a proliferative disorder caused or characterized by a proliferation of cells which have lost susceptibility to normal growth control. Cancers of the same tissue type usually originate in the same tissue, and may be divided into different subtypes based on their biological characteristics. Four general categories of cancer are carcinoma (epithelial cell derived), sarcoma (connective tissue or mesodermal derived), leukemia (blood-forming tissue derived) and lymphoma (lymph tissue derived). Over 200 different types of cancers are known, and every organ and tissue of the body can be affected. Specific examples of cancers that do not limit the definition of cancer can include melanoma, leukemia, astrocytoma, glioblastoma, retinoblastoma, lymphoma, glioma, Hodgkin's lymphoma, and chronic lymphocytic leukemia. Examples of organs and tissues that may be affected by various cancers include pancreas, breast, thyroid, ovary, uterus, testis, prostate, pituitary gland, adrenal gland, kidney, stomach, esophagus, rectum, small intestine, colon, liver, gall bladder, head and neck, tongue, mouth, eye and orbit, bone, joints, brain, nervous system, skin, blood, nasopharyngeal tissue, lung, larynx, urinary tract, cervix, vagina, exocrine glands, and endocrine glands. Alternatively, a cancer can be multicentric or of unknown primary site (CUPS). In some embodiments, the method is used to treat a subject having melanoma or osteosarcoma.

In some embodiments, the β-glucans are administered to treat metastatic cancer. As used herein, "metastasis" refers to the ability of cells of a cancer (e.g. a primary tumor, or a metastatic tumor) to be transmitted to other locations in the subject (i.e., target organs) and to establish new tumors at such locations. The most common places for the metastases to begin are referred to as the primary cancer, and include are the lung, breast, skin, colon, kidney, prostate, pancreas, liver, and cervix. There is a propensity for certain tumors to seed in particular organs. For example, prostate cancer usually metastasizes to the bones. In a similar manner, colon cancer tends to metastasize to the liver. Stomach cancer often metastasizes to the ovary in women. In some embodiments, the present invention is used to treat the metastasis originating from breast cancer, prostate cancer, or lung cancer primary tumors. The cells capable of forming metastatic cancer are circulating cancer cells are those that move within the bloodstream, as opposed to cancer cells present at a fixed location, such as a solid tumor.

In some embodiments, the method is used to treat cancer that has developed immune tolerance. Immune tolerance is the state in which cancer cells exhibit decreased immunogenicity or the establishment of an immunosuppressive state within the tumor microenvironment, thereby diminishing the ability of the immune system to attack the cancer cells. Immune tolerance is a frequent problem in cancer treatment, in part because the cancer cells have a large number of self-antigens, for which immune tolerance is necessary. Makkouk A., Weiner G., Cancer Res., 75(1):5-10 (2015).

Methods in accordance with the invention include administration of the β-glucan alone, or combination therapies wherein the subject is also undergoing one or more cancer therapies selected from the group consisting of surgery, chemotherapy, radiotherapy, thermotherapy, immunotherapy, hormone therapy and laser therapy. Combination therapy will typically include treatment with one or more of chemotherapeutics, tumor-targeting antibodies; adoptive transfer of immune cells (i.e., adoptive immunotherapy); pro-inflammatory cytokines, and the like. Combination therapy can also include conventional therapy, including, but not limited to, antibody administration, vaccine administration, administration of cytotoxic agents, thermoablation, cryoablation, and radioablation.

The invention includes, in part, co-administering a β-glucan with another pharmaceutical agent. The two components may be co-administered simultaneously or sequentially. Simultaneously co-administered components may be provided in one or more pharmaceutical compositions. Sequential co-administration of two or more components includes cases in which the components are administered so that both components are simultaneously bioavailable after both are administered. Regardless of whether the components are co-administered simultaneously or sequentially, the components may be co-administered at a single site or at different sites.

Examples of chemotherapeutic agents that can be co-administered with β-glucan for cancer treatment include alkylating agents, antimetabolites, natural products, hormones and antagonists, and miscellaneous agents. Examples of alkylating agents include nitrogen mustards such as mechlorethamine, cyclophosphamide, ifosfamide, melphalan (L-sarcolysin) and chlorambucil; ethylenimines and methylmelamines such as hexamethylmelamine and thiotepa; alkyl sulfonates such as busulfan; nitrosoureas such as carmustine (BCNU), semustine (methyl-CCNU), lomustine (CCNU) and streptozocin (streptozotocin); DNA synthesis antagonists such as estramustine phosphate; and triazines such as dacarbazine (DTIC, dimethyl-triazenoimidazolecarboxamide) and temozolomide. Examples of antimetabolites include folic acid analogs such as methotrexate (amethopterin); pyrimidine analogs such as fluorouracin (5-fluorouracil, 5-FU, 5FU), floxuridine (fluorodeoxyuridine, FUdR), cytarabine (cytosine arabinoside) and gemcitabine; purine analogs such as mercaptopurine (6-niercaptopurine, 6-MP), thioguanine (6-thioguanine, TG) and pentostatin (2'-deoxycoformycin, deoxycoformycin), cladribine and fludarabine; and topoisomerase inhibitors such as amsacrine. Examples of natural products include vinca alkaloids such as vinblastine (VLB) and vincristine; taxanes such as paclitaxel (Abraxane) and docetaxel (Taxotere); epipodophyllotoxins such as etoposide and teniposide; camptothecins such as topotecan and irinotecan; antibiotics such as dactinomycin (actinomycin D), daunorubicin (daunomycin, rubidomycin), doxorubicin, bleomycin, mitomycin (mitomycin C), idarubicin, epirubicin; enzymes such as L-asparaginase; and biological response modifiers such as interferon alpha and interleukin 2. Examples of hormones and antagonists include luteinizing releasing hormone agonists such as buserelin; adrenocorticosteroids such as prednisone and related preparations; progestins such as hydroxyprogesterone caproate, medroxyprogesterone acetate and megestrol acetate; estrogens such as diethylstilbestrol and ethinyl estradiol and related preparations; estrogen antagonists such as tamoxifen and anastrozole; androgens such as testosterone propionate and fluoxymesterone and related preparations; androgen antagonists such as flutamide and bicalutamide; and gonadotropin-releasing hormone analogs such as leuprolide. Examples of miscellaneous agents include thalidomide; platinum coordination complexes such as cisplatin (czs-DDP), oxaliplatin and carboplatin; anthracenediones such as mitoxantrone; substituted ureas such as hydroxyurea; methylhydrazine derivatives such as procarbazine (N-methylhydrazine, MIH); adrenocortical suppressants such as mitotane (o,p'-DDD) and aminoglutethimide; RXR agonists such as bexarotene; and tyrosine kinase inhibitors such as imatinib.

In some embodiments, the cancer is further treated with adoptive immunotherapy. Adoptive immunotherapy is a form of immunotherapy in which lymphocytes taken from a patient are grown in large numbers, stimulated, activated, and infused back into the patient. Adoptive immunotherapy can use a variety of different immune cells, including lymphokine-activated killer (LAK) cells, tumor-infiltrating lymphocytes (TILs), and immune effector cells such as T-lymphocytes (e.g., cytokine activated T-cells). See Ruella M, Kalos M., Immunol Rev., 257(1):14-38 (2014). For example, in some embodiments, cancer treatment using β-glucan can be combined with adoptive transfer of T-lymphocytes (e.g., tumor draining lymph node T-lymphocytes).

In some embodiments, β-glucan administration is combined with substances that activate T-cells, or inflammatory cytokines. Examples of substances that activate T-cells include IL-2, Opdivo (nivozumab, PD-1 inhibitor, by Bristol-Myers); Keytruda (pembrolizumab, PD-1 inhibitor, by Merck & Co.), Tecentriq (atezolizumab, PD-L1 inhibitor, by Genentech), Imfinzi (durvalumab, PD-L1 inhibitor, by AstraZeneca), or Bavencio (Avelumab, PD-L1 inhibitor, by EMD Serono Inc.). Examples of inflammatory cytokines include CCL3, CC14, TNF-α, and interferon-γ. A variety of small molecule inhibitors of the TGF-β type 1 receptor can also be used to stimulate inflammation.

Once disease is established and a treatment protocol is initiated, evaluation of the cancer can be repeated on a regular basis to evaluate whether the cancer cells in the subject begin to show resistance to the therapy. The results obtained from successive assays may be used to show the efficacy of treatment over a period ranging from several days to months. Accordingly, the invention is also directed to methods for monitoring a therapeutic regimen for treating a subject having cancer by β-glucan administration. A comparison of the total cell number (and/or blood cell count) prior to and during therapy indicates the efficacy of the therapy. Likewise, a comparison of the severity of the side effects of chemotherapy prior to and during β-glucan therapy indicates the efficacy of β-glucan therapy. Therefore, one skilled in the art will be able to recognize and adjust the therapeutic approach as needed.

Immunostimulation Using β-(1,3)-(1,4) Glucan

In another aspect, the present invention provides a method of immunostimulation that includes administering an effective amount of a β-(1,3)-(1,4) glucan to a subject. "Immunostimulation" as used herein refers to stimulation the immune system by inducing activation or increasing activity of any of its components. In some embodiments, immunostimulation includes stimulation of an inflammatory response. In other embodiments, immunostimulation includes stimulation of the cellular immune system. For example, in some embodiments, immunostimulation includes macrophage activation, while in further embodiments the immunostimulation includes T-cell activation.

Immunostimulation can be beneficial for a subject suffering from suppressed immunity. Impairment of any of the major components of the immune system (T-cells, B-cells phagocytes, complement) may result in suppressed immunity. Immune defects can arise from intrinsic or heritable defects of lymphoid elements, failure of normal cellular differentiation, diseases such as cancer or viral infection, or other acquired causes. Clinical impairment of immunity is expressed as a marked susceptibility to opportunistic and pathogenic organisms which are difficult to control and by an increased risk of malignancy, allergy and autoimmune disease. In some embodiments, the method of immunostimulation is used to stimulate the immune system of a subject that has cancer, while in further embodiments the subject has cancer that has developed immune tolerance.

The method of immunostimulation can include administration of any of the types of β-(1,3)-(1,4) glucan described herein. In some embodiments, the β-(1,3)-(1,4) glucan is oat-derived. In further embodiments, the β-(1,3)-(1,4) glucan has a linear chain structure. In further embodiments, the β-(1,3)-(1,4) glucan having a weight from 50 to 500 kDa; a molecular weight from 75 to 400 kDa; a molecular weight from 100 to 300 kDa; a molecular weight from 150 to 250 kDa; a molecular weight from 175 to 225 kDa; or a molecular weight from 190 to 210 kDa.

Administration and Formulation

The β-glucan (i.e., β-(1-3)-(1-4) glucan), any additional agents (e.g., anticancer agents), or a combination thereof, may be formulated into a pharmaceutical composition. In some embodiments, the β-glucan and the pharmaceutical agent may be provided in a single formulation. In other embodiments, the β-glucan and the pharmaceutical agent may be provided in separate formulations. A pharmaceutical composition may be formulated in a variety of and/or a plurality forms adapted to one or more preferred routes of administration. Thus, a pharmaceutical composition can be administered via one or more known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). A pharmaceutical composition, or a portion thereof, can be administered to a mucosal surface, such as by administration to, for example, the nasal or respiratory mucosa (e.g., by spray or aerosol). A pharmaceutical composition, or a portion thereof, also can be administered via a sustained or delayed release.

A formulation may be conveniently presented in unit dosage form and may be prepared by methods well known in the art of pharmacy. Methods of preparing a composition with a pharmaceutically acceptable carrier include the step of bringing the β-glucan and/or the pharmaceutical agent into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

The β-glucan, the pharmaceutical agent, and/or the combination of both components may be provided in any suitable form including but not limited to a solution, a suspension, an emulsion, a spray, an aerosol, or any form of mixture. The composition may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives including such as, for example, an adjuvant, a skin penetration enhancer, a colorant, a fragrance, a flavoring, a moisturizer, a thickener, and the like.

In some embodiments, the method can include administering sufficient β-glucan to provide a dose of, for example, from about 100 ng/kg to about 50 mg/kg to the subject, although in some embodiments the methods may be performed by administering the β-glucan in a dose outside this range. In some embodiments, the method includes administering sufficient β-glucan to provide a dose of from about 10 μg/kg to about 5 mg/kg to the subject, for example, a dose of about 4 mg/kg.

Alternatively, the dose may be calculated using actual body weight obtained just prior to the beginning of a treatment course. For the dosages calculated in this way, body surface area ($m^2$) is calculated prior to the beginning of the treatment course using the Dubois method: $m^2 = (wt\ kg^{0.425} \times height\ cm^{0.725}) \times 0.007184$. In some embodiments, therefore, the method can include administering sufficient β-glucan to provide a dose of, for example, from about 0.01 mg/m$^2$ to about 10 mg/m$^2$.

Pharmaceutically acceptable carriers useful for formulating β-glucan for administration to a subject are well known in the art and include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the physico-chemical characteristics of the therapeutic agent and on the route of administration of the composition, which can be, for example, orally or parenterally such as intravenously, and by injection, intubation, or other such method known in the art. The pharmaceutical composition also can contain a second (or more) compound(s) such as a diagnostic reagent, nutritional substance, toxin, or therapeutic agent, for example, a cancer chemotherapeutic agent and/or vitamin(s).

The present invention is illustrated by the following example. It is to be understood that the particular example, materials, amounts, and procedures are to be interpreted broadly in accordance with the scope and spirit of the invention as set forth herein.

EXAMPLE

Systemic Administration of β-glucan of 200 kDa Modulates Melanoma Microenvironment and Suppresses Metastatic Cancer Previous studies on BG34 have proposed two mechanisms for their anti-cancer action. In vitro studies on low molecular weight oat β-(1-3)-(1-4)-glucans showed that they could mediate tumor cell apoptosis via direct cytotoxic effect. Choromanska et al., Int J Biol Macromol, 80: p. 23-8 (2015). A study on barley β-(1-3)-(1-4)-glucans suggested that barley BG34 alone did not mediate any in vivo anticancer action in a murine neuroblastoma model; however, barley BG34 in combination with an anti-ganglioside monoclonal antibody mediated enhanced inhibitory effect on cancer growth. Cheung, N. K., Modak S., Clin Cancer Res, 8(5): p. 1217-23 (2002). In this example, the inventors show that BG34 with a molecular weight of 200 kDa (BG34-200) does not mediate direct cytotoxicity to murine and human melanoma cells. Instead, systemic administration of BG34-200 results in profound inhibition of malignant primary melanoma B16F10 as well as lung metastases. The superior antitumor efficacy of BG34-200 was supported by enhanced T cell activation both locally at tumor site and regionally within the tumor-draining lymph node. The results indicate that BG34-200 alters immune signature and promotes the development of highly potent antitumor immune responses by modulating the tumor microenvironment.

Materials and Methods

BG34 Sample Preparation and Characterization

Figure 2:
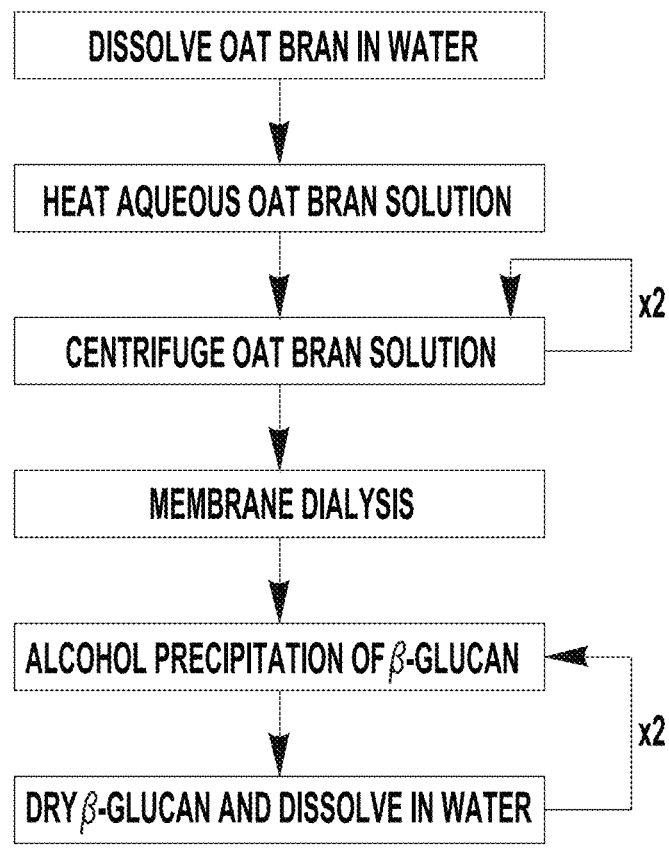
FIG. 2 provides a flowchart showing the steps in a manufacturing process for obtaining β-(1,3)-(1,4) glucan.

Isolation, purification and fractionation of β-(1-3)-(1-4)-glucans (BG34s) from oat brans was carried out as previously described. Zhang, M., Kim, J. A., Int J Biochem Cell Biol, 44(6): p. 914-27 (2012). The process for manufacturing BG34s 100 is shown in FIG. 2. In the first step 10, oat bran is added to distilled water to provide a 1% w/w solution. The aqueous solution of oat bran is then heated to 85° C. under constant stirring for 3-4 hours 20. The solution is then cooled to room temperature, and centrifuged at ~10,000 rpm for about 25 minutes 30. The supernatant is collected, and then the precipitate is added into the supernatant under constant stirring, and the solution is again centrifuged at ~10,000 rpm, after which this step is repeated one more time. The precipitate is then dissolved in distilled water to provide a 5% w/w solution, which is then subject to membrane filtration and centrifugation 40 to remove salt and small molecules. The concentrated solution is then diluted to again provide a 5% w/w solution, which is then precipitated using 70% alcohol 50. The precipitate is collected and then oven dried at 55-60° C., after which it is re-dissolved in distilled water to provide a 5% w/w solution 60. Steps 50 and 60 are repeated twice to give the final BG34 product.

The chemical structure, molecular weight and polydispersity of BG34 samples were characterized by Infrared Spectroscopy (IR), $^{13}C$ and $^{1}H$ Nuclear Magnetic Resonance Spectroscopy (NMR) and Gel Permeation Chromatography (GPC). BG34 of 10, 200 and 500 kDa (BG34-10, BG34-200 and BG34-500) were used in this study. Endotoxin of the glucan samples were tested by Endosafe PTSTM system (Charles River, Skokie, Ill.).

Mice and Cell Lines

Male, age-matched wild-type (WT) C57BL/6J, CD11b-knockout (CD11b-KO) (B6.129S4-Itgam$^{tm1Myd}$/J), IFN-γ-KO (B6.129S7-IFNg$^{tm1Ts}$/J), CD11c-DTR (B6.FVB-Tg(Itgax DTR/EGFP)57Lan/J) transgenic mice on a CD45.2 background (8-10 weeks), C57BL/6J (B6.SJL-Ptprc$^a$Pepc$^b$/BoyJ) mice on a CD45.1 background (8-10 weeks), and PMEL (B6.CgThy1$^a$/CyTg(TcraTcrb)8Rest/J) mice were purchased from the Jackson Laboratory (Bar Harbor, Me.). Nude mice were from the Animal Research Center of Case Western Reserve University. CD11c-venus mice were from Dr. Alex YC Huang's lab at Case Western Reserve University. To generate CD11c-depleted mouse model, bone marrow (BM) chimeras were generated by reconstitution with BM cells from CD11c-DTR mice as described. Yi et al., Blood, 113(23): p. 5819-28 (2009). All experimental procedures were conducted according to the protocols approved by Case Western Reserve University Animal Research Center. B16F10 and A375 cells were purchased from ATCC. Osteosarcoma K7M2-Luc2 cells were from Dr. Alex YC Huang's lab. Cells were periodically authenticated by morphologic inspection and animal grafting to assess tumor histology and ability to grow and metastasize. All cell lines were maintained in DMEM (Invitrogen, Carlsbad, Calif.) supplemented with 10% fetal bovine serum (Invitrogen, Carlsbad, Calif.) and routinely examined for mycoplasma contamination using a PCR-based mycoplasma detection kit.

Reagents and Antibodies (Abs)

For fluorescence-activated cell sorting (FACS) analysis, anti-mouse CD45-V450 (30F11), CD11b-PE (M1/70), CD19-PE-Cy7 (1D3), F4/80-AF647 (T45-2342), CD4-AF488 (RM45), CD8-PE (53-6.7), CD86-V450 (GL1), CD11b-PE, CD45-PerCp (30-F11), CD8-V450 (53 6.7), CD62L-AF700 (MEL-14), CD44-PE (1M7), CD27-APC (3A10), CD19-PE-Cy7 (1D3), CD5-PE (53.7.3), B220-PE (RA3-6B2), NK1.1-AF700 (PK136), CD11c-FITC (HL3), CD49b APC (DX5), CD45.1-PE (A20), CD45.2-APC (104), IFN-γ-PE (XMG1.2), IFN-γ-AF647 (XMG1.2) and IL-2-PE (JES6-5H4) were purchased from BD Biosciences (San Jose, Calif.), CD3 Percp (17A2) and B220-AF488 (RA3-6B2) were purchased from R&D Systems (Minneapolis, Minn.), CD3-AF405 (C415.9A) was purchased from Santa Cruz Biotechnology (Dallas, Tex.), GR1-APC (RB5-8C5) was purchased from Miltenyi Biotec (San Diego, Calif.), Ly6G-FITC (1A8) and granzyme B-PE (MGZB) were purchased from ThermoFisher Scientific (Waltham, Mass.). Mouse IFN-γ and IL-2 ELISA kits were purchased from R&D Systems (Minneapolis, Minn.). FITC-conjugated latex beads were purchased from Sigma Aldrich (St Louis, Mo.). Thymidine incorporation assay kit was purchased from ThermoFisher Scientific (Waltham, Mass.). Mouse recombinant GM-CSF and M-CSF proteins were purchased from R&D Systems. GP10025-33 peptide was gifted from Prof. Shawn Wang (Virginia Commonwealth University). Cytofix/Cytoperm and fixation buffers were purchased from BD Biosciences (San Jose, Calif.). Cytometric bead array mouse inflammation kit (TNF-α, IL-6, IL-10, MCP-1, IFN-γ and IL-12p70) was purchased from BD Biosciences (San Jose, Calif.).

Tumor Study

B16F10 tumors were established by injecting $5\times10^5$ B16F10 tumor cells to the flank of mice. Four days after tumor cell inoculation, mice were randomized and received intraperitoneally (i.p.) injected BG34 solutions at ~25 mg/kg. Mice were treated by BG34 of three different molecular weight (10, 200 and 500 kDa), respectively, to determine effect of molecular weight on antitumor activity. Mice treated with PBS or dextran served as controls. Treatments were administered daily for five days, or twice or three times a week. Tumor growth was monitored by measuring the length of short (l) and long (L) diameters (volume=$l^2 \times L/2$) as described. Fisher et al., J Clin Invest, 121(10): p. 3846-59 (2011). Animals were euthanized when tumors reached 10% of the total body weight. To generate experimental lung metastases, mice were injected intravenously (i.v.) with $1\times10^5$ B16F10 tumor cells. For analysis of leukocyte infiltration, tumor tissues were digested with tumor dissociation kit (Miltenyi Biotec, San Diego, Calif.), and cell suspensions were filtered through a 40-μm cell strainer (ThermoFisher Scientific, Waltham, Mass.) as described. Yi et al., Cancer Res, 71(21): p. 6611-20 (2011).

For osteosarcoma model, tumors were established by injecting $5\times10^5$ K7M2-luc2 cells i.v. to Balb/c mice. Mice received intranasal administered BG34-200 weekly for 7 weeks at 25 mg/kg. Mice treated with PBS served as control. Tumor growth and metastasis were monitored by non-invasive bioluminescent imaging. Images collected via an IVIS Spectrum instrument (Perkin Elmer, Waltham, Mass.) using their proprietary acquisition and data analysis software (Living Image v4.5).

Real Time PCR

Total RNA was extracted using TRIzol Reagent (Invitrogen Corp., Carlsbad, Calif.). Reverse transcriptional and real-time reverse transcriptional PCR were performed using primers and FAM-labeled probe sets from Applied Biosystems (Carlsbad, Calif.). Gene expression was quantified relative to the expression of β-actin, and normalized to that measured in PBS-treated group by standard $1^{(-\Delta\Delta CT)}$ calculation.

Expansion and function assay of bone marrow derived macrophages (BM-Ms) and dendritic cells (BM-DCs)

BM-Ms and BM-DCs were developed by culturing mouse bone marrow cells using MCSF (20 ng/mL) and GM-CSF (20 ng/mL), respectively.

For BM-M cultures, BG34-200 was added to BM-M cultures at 0, 1, 5 and 20 μM. Proportions of CD11b$^+$F4/80$^+$ cells on day 0, 4, 7 and 14 were quantified by FACS. The day 14 BM-Ms were co-cultured with FITC-conjugated beads for 6 hours. After co-culture, BM-Ms were washed to remove beads and analyzed by FACS to quantify macrophage phagocytosis of fluorescent beads. The day 14 BM-Ms were also co-cultured with B16F10 cells at 5:1 ratio. After co-culture with tumor cells, cell conditioned media were harvested to determine the concentration of inflammatory cytokines using cytometric bead array mouse inflammation kit (TNF-α, IL-6, IL-10, MCP-1, IFN-γ and IL-12p70).

For BM-DC cultures, BG34-200 was added to BM-DC cultures at 0, 1, 5 and 20 µM. BG34-200-treated macrophage conditioned medium at different dilution were also added to BMDC cultures. For these cultures, proportions of CD11c$^+$ cells on day 0, 4, 7 and 14 were quantified by FACS. Function of these BM-DCs were determined by T cell activation assay. BMDCs were pulsed with 25 µg/mL of gp100$_{25-33}$ peptides. Serially diluted cells were incubated with $1 \times 10^5$ purified PMEL CD8+ T cells for 3 days. 3H-thymidine ($^3$H-TdR, 0.5 µCi/well) was added to the wells for the final 16 h of culture. T cell proliferation was measured using $^3$H-TdR incorporation assays.

T Cell Activation Assays

For intracellular cytokine staining of T cells, gp100$_{25-33}$ peptide (1 µg/mL)-stimulated splenocytes or tumor draining lymph node cells (TDLNs) from treated or untreated group were treated with PMA (10 nM) plus ionomycin (1 µM) in the presence of brefeldin A (5 µg/mL) for 5 h. Cells were stained with anti-CD8 Abs and permeabilized using a Cytofix/Cytoperm kit (BD Biosciences). The cells were then stained with Abs for IFN-γ or granzyme B.

FACS Analysis

Multi-parameter FACS analysis of various immune cell phenotype was performed by staining with suitable monoclonal Abs. Flow cytometric analysis was performed on BD LSRII flow cytometer (BD Biosciences, San Jose, Calif.); compensation and analysis were performed using Winlist 7.0 (Verity Software House, Inc. Topsham, Me.).

Statistical Analysis

Data are expressed as mean±S.D. values. Statistical significance between groups within experiments was determined by the Student's t-test or ANOVA test. Values of p<0.05 were considered to be statistically significant.

Results

Systemic Treatment Using BG34-200 Generates Potent Systemic Anti-Melanoma Response The inventors have previously engineered BG34 of molecular weight 10 kDa (BG34-10), 200 kDa (BG34-200) and 500 kDa (BG34-500) and observed that BG34-200 could mediate the most effective uptake by murine bone marrow macrophages (BMM). Zhang, M., Kim, J. A., Int J Biochem Cell Biol, 44(6): p. 914-27 (2012). Compared to BG34-10, BG34-500, and PBS and dextran controls, intraperitoneal (i.p.) treatment of wild type (WT) C57BL/6 mice bearing established subcutaneous B16F10 tumor with BG34-200 resulted in a potent inhibition of tumor growth (FIGS. 3A, B and C), leading to significantly prolonged survival of the mice (FIG. 3D). They also examined the dosing effects by treating tumor-bearing mice with BG34-200 twice, three times or five times a week. Administration of BG34-200 three times or five times a week i.p. resulted in the most effective therapeutic benefits. Mice that responded to BG34-200 treatment did not show any noticeable autoimmune symptoms (e.g., vitiligo) or apparent toxicities in major organs.

In order to evaluate whether BG34-200 treatment generated systemic protective immunity, the efficacy of BG34-200 was examined in an experimental lung metastasis model by injecting mice with B16F10 melanoma i.v. (FIG. 3E). Indeed, mice treated with BG34-200 harbored the fewest lung metastases as compared to PBS treatment group (FIGS. 3F and G).

BG34-200 Treatment Alters Immune Signature of Melanoma Microenvironment and Induces T-Cell Activation in the Tumor Sites Next, the inventors determined BG34-200 induced changes in immune cellular composition within melanoma tumor microenvironment by FACS. Frequencies of intratumoral CD45$^{high}$F4/80$^+$CD11b$^-$SSC$^{high}$ macrophages and CD11c$^+$B220$^+$ DCs were significantly increased, while frequencies of intratumoral granulocytes were significantly decreased in BG34-200-treated mice as compared to those receiving PBS (FIGS. 4A and B). They observed similar BG34-200-induced increases in CD11c$^+$ DCs when CD11c-venus mice were used to examine DC infiltration in primary B16F10 tumors (FIG. 4C). BG34-200 treatment also resulted in a significant increase in the frequency of tumor-infiltrating effector T cells (both CD4$^+$CD62L$^-$ CD44$^+$ and CD8$^+$ CD62L$^-$CD44$^+$) and memory T cells (CD4$^+$CD62L$^+$ CD44$^+$) (FIGS. 4D and E), as determined by fluorescence staining and FACS analysis. Importantly, tumor-infiltrating CD8$^+$ cells from BG34-200 treated mice expressed high levels of IFN-γ and granzyme B (FIG. 4F).

Next, the inventors examined multiple gene expression profiles of tumor tissues by qRT-PCR. They observed that BG34-200 treatment significantly increased the mRNA expression of IFN-γ, TNF-α, CXCL9, CXCL10, PDL-1 and IRF-1 (FIG. 4G), suggesting that BG34-200 treatment resulted in a "pro-inflammatory" tumor microenvironment. In addition, mRNA expression of iNOS was increased while that of arginase 1 was decreased in BG34-200 treated mice as compared to PBS control (FIG. 4G), suggesting a strong M1-like activation among tumor-associated macrophages as a result of exposure to BG34-200.

BG34-200 Treatment Augments Systemic Activation of Melanoma-Specific T Cells

Figure 5A:
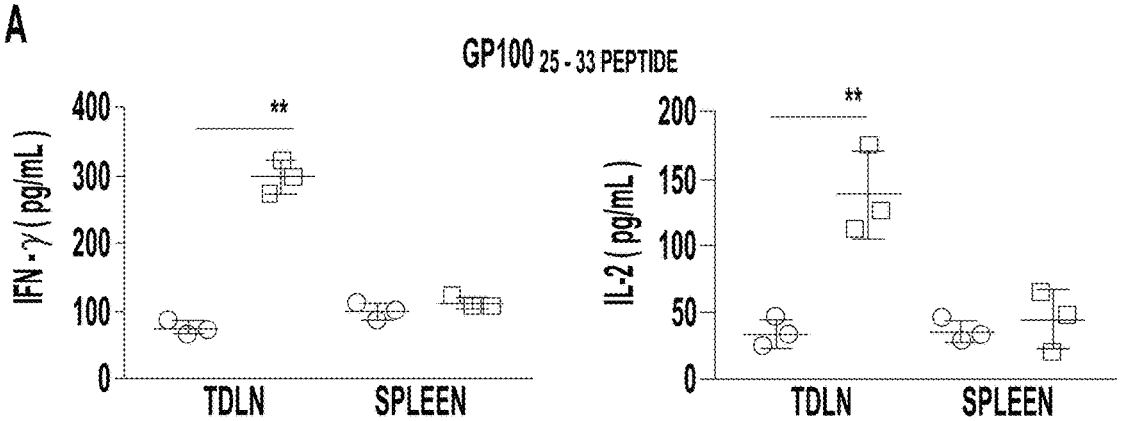
FIGS. 5A-C provides graphs showing BG34-200 treatment augments systemic activation of T cells recognizing melanoma antigen. (A) Splenocytes or TDLN cells were stimulated with gp10025-33 peptide. IFN-γ and IL-2 levels in the culture media were assessed using ELISA. (B) Frequencies of CD3, CD4, CD8 T cells and their expression of CD62L and CD44 in spleen and TDLN were determined by FACS analysis. (C) TDLN cells were subjected to intracellular cytokine staining for determining the frequency of gp10025-33-specific T cells. (A) and (B) were graphed as means±SD. Each data point represents one of three replicates of samples from individual TDLN or spleen. *p<0.05, **p<0.01. Significance was determined using Student's t test.
Figure 5B:
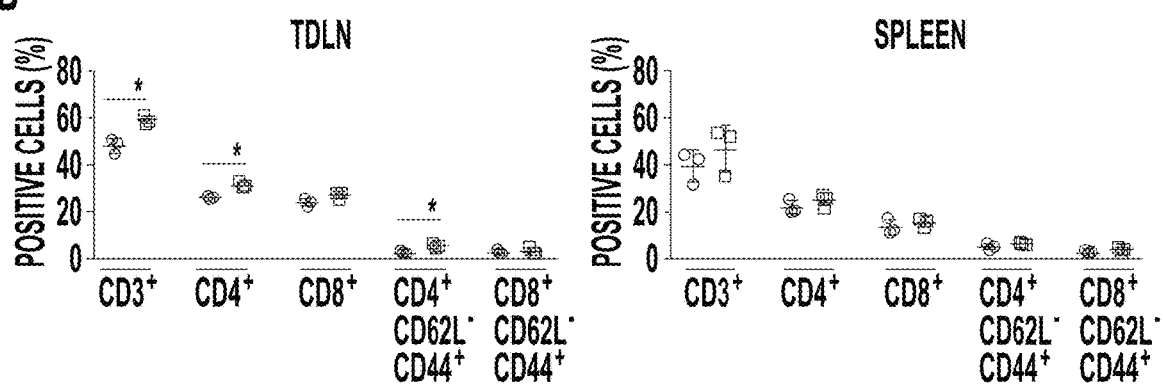
Figure 5C:
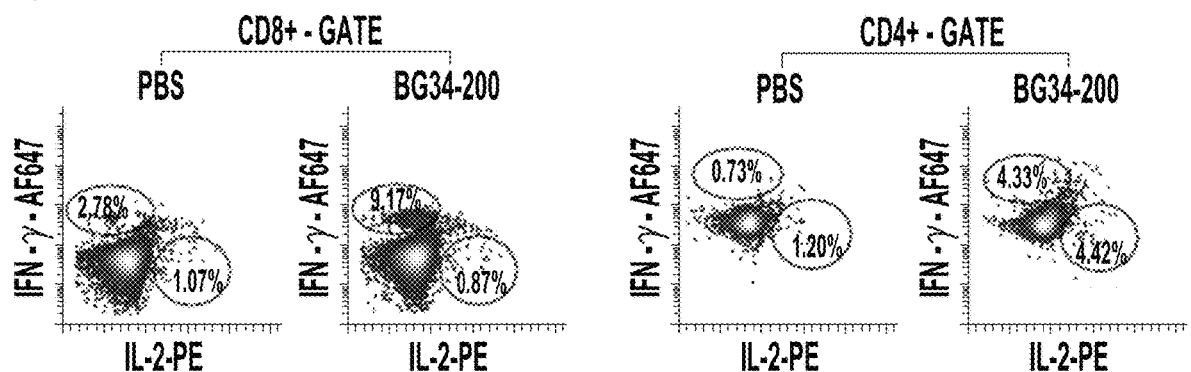

In addition to immune stimulation in the tumor site, BG34-200 treatment led to a strong systemic activation of tumor-reactive T cells, as indicated by enhanced IFN-γ and IL-2 production by T cells from the tumor draining lymph nodes (TDLNs) upon re-stimulation with H-2D$^b$-restricted gp100$_{25-33}$ in vitro, as determined by ELISA (FIG. 5A). Increased frequencies of effector memory and central memory T cells in was observed in TDLNs (FIG. 5B). Intracellular cytokine staining also showed a higher frequency of IFN-γ and IL-2 production among gp100$_{25-33}$-specific CD8$^+$ T cells (FIG. 5C).

CD11b$^+$, CD11c$^+$, T cells and IFN-γ are required for BG34-200 induced anti-tumor responses Given the robust BG34-200-induced anti-melanoma response, the inventors sought to determine the effects of BG34-200 on tumor cells and various immune subsets in vitro. First, direct co-culture of BG34-200 with murine melanoma B16F10 cells or human melanoma A375 cells did not directly affect tumor cell proliferation, as determined by MTT assay. Next, direct co-culture of BG34-200 with murine TDLNs or human melanoma draining lymph nodes in the presence of IL-2 and CD3/CD28 activating beads in vitro demonstrated that BG34-200 did not directly affect T cell expansion, CD4/CD8 ratio or IFN-γ/IL-2 production.

A previous study by the inventors demonstrated that BG34 could directly engage macrophages via binding to CD11b receptor (Chan, J Hematol Oncol, 2: p. 25 (2009)). In view of this earlier work, the inventors co-cultured BG34-200 with bone marrow-derived primary macrophages in vitro. Although direct culture with BG34-200 did not affect macrophage expansion, exposure to BG34-200 significantly enhanced the phagocytic activity of macrophages (FIG. 6A) and their secretion of TNF-α (FIG. 6B). To confirm the important functional roles of macrophages and CD11b in BG34-200 mediated effect, mice that lack CD11b$^+$ myeloid cells (CD11b-KO) were used to define the potential involvement of CD11b in BG34-200-induced anti-melanoma immune responses. The results showed that lack of CD11b$^+$ cells abrogated the in vivo therapeutic efficacy of BG34-200 (FIG. 6C). Correspondingly, mRNA levels of CCL3, CCL4, CCR5, CXCL9, CXCL10, IFN-γ, PDL-1 and TNF-α in the primary tumor sites were all significantly reduced in CD11b-KO mice (FIG. 6D).

Considering the important role of DCs in coordinating innate and adaptive immune responses, direct co-culture of BG34-200 with BMDCs was performed in vitro. Neither the expansion of BMDCs nor their antigen presenting capability was affected (FIG. 7A). However, when co-cultured with BG34-200-treated macrophage-conditioned medium, BMDCs appeared to exhibit enhanced antigen presenting capability in a dose-dependent manner, as determined by 3H-thymidine incorporation assay of PMEL CD8$^+$ T cell activation driven by gp100$_{25-33}$-pulsed BMDCs (FIGS. 7A and B). Finally, CD11c-DTR transgenic mice were utilized to define the potential involvement of CD11c$^+$ DCs in BG34-200 induced anti-melanoma immune responses. The inventors developed bone marrow chimera in which WT mice were reconstituted with the BM from CD11c-DTRtg mice. The results showed that depletion of CD11c+ cells in diphtheria toxin (DTx)-treated chimera mice abrogated the therapeutic efficacy of BG34-200 (FIG. 7C) as compared to WT mice receiving PBS and BG34-200 (FIG. 6C, left).

Figure 8A:
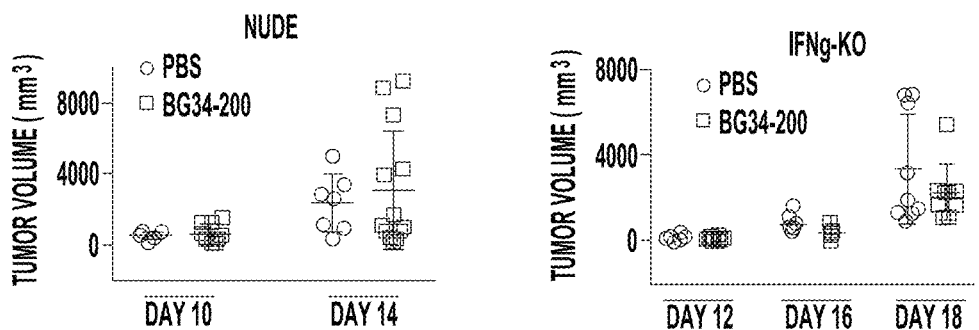
FIGS. 8A-B provides graphs showing Lymphocytes and IFN-γ are essential for BG34-200-induced antitumor responses. (A) Tumor volumes in nude (left) and IFN-γ-KO mice (right) bearing established B16F10 with or without BG34-200 treatment. Tumor volumes at different time points for individual animals in each group were graphed. n=9 per group. (B) RNA expression in B16F10 tumor tissues from nude mice (up) and IFN-γ-KO mice (down) with or without BG34-200 treatment. Each data point represents one of three replicates of RNA samples from individual tumor. *p<0.05, **p<0.01. Significance was determined by two-way ANOVA with Student's t test.
Figure 8B:
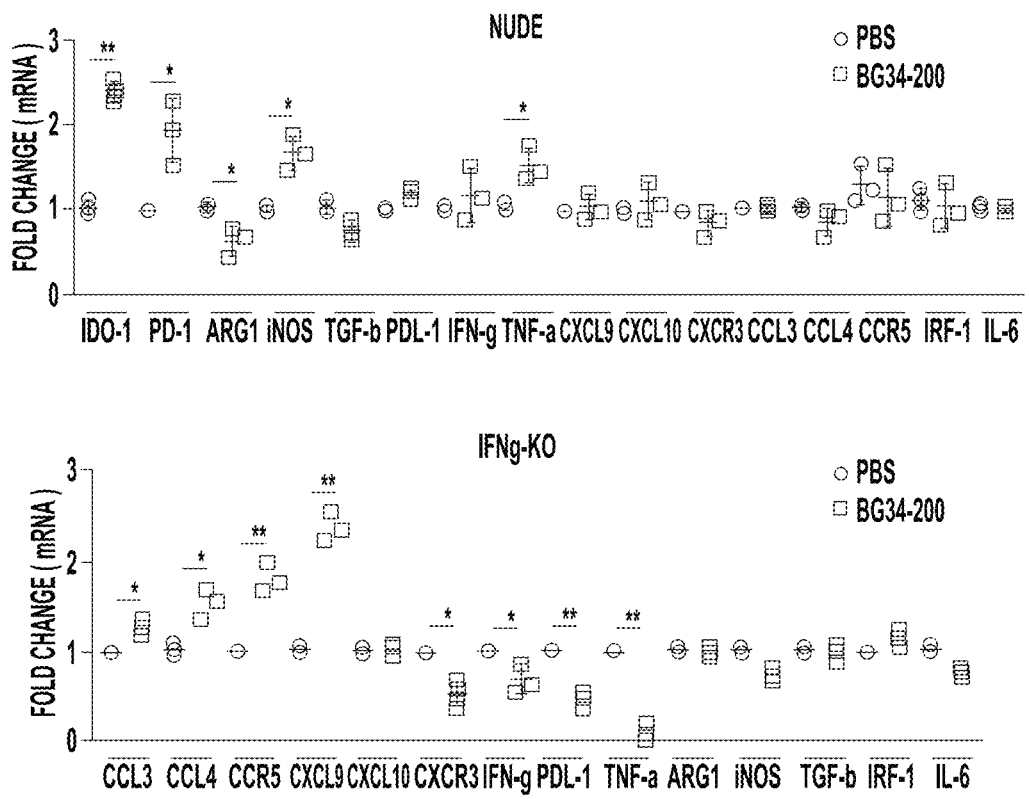
Figure 14A:
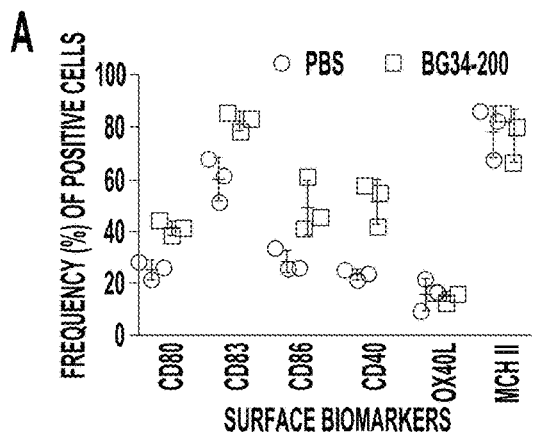
FIGS. 14A-D provides graphs showing that the BG34-200 transportation to TDLN associated with T-cell activation and mediation of long term antitumor immune responses. FACS analysis of surface biomarkers (A) and intracellular biomarkers (B) of the CD11b$^+$CD11c$^+$ cells sorted from TDLNs of mice receiving PBS or BG34-200. (C) FACS analysis of cell proliferation (CFSE) and CD44 expression of the CD8-enriched T cells of TDLNs of mice receiving PBS or BG34-200 after re-stimulation with H-2D$^b$-resticted gp100$^{25-33}$ peptide. Results indicated the generation of melanoma specific effector T-cell in TDLN of mice receiving BG34-200 as compared to those receiving PBS. (D) BG34-200 treatment resulted in protective response in mice receiving a secondary tumor challenge. Mice that were sensitized with tumor cell (8,000 cells/mouse) on left flank and received BG34-200 treatment showed a complete regression of tumor. The tumor free mice were re-challenged with half million B16F10 cells on the right flank and tumor growth was recorded. Tumor free mice receiving PBS injection were re-challenged with same dose of B16F10 and served as control. n=9. (A) and (B), data were graphed as mean±SD. Each data point represents pooled samples from three mice. FACS graphs represent one of three replicates of cell samples. (D) n=9. *, p<0.05. **, p<0.01. Significance was determined by two-way ANOVA with student's t-test.
Figure 14B:
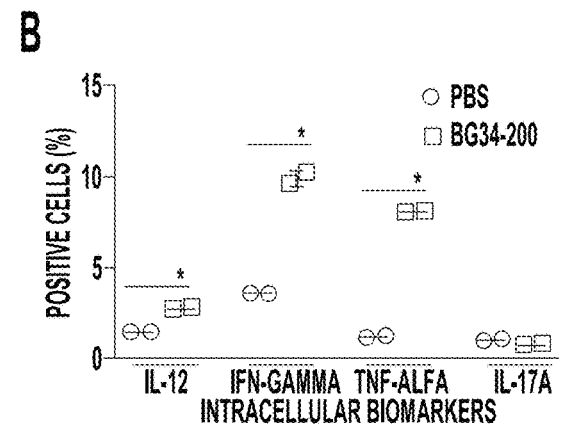
Figure 14C:
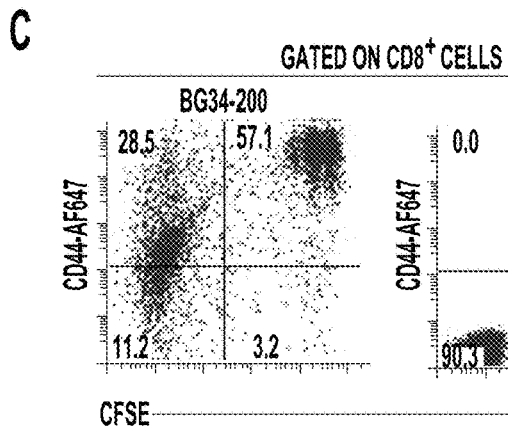
Figure 14D:
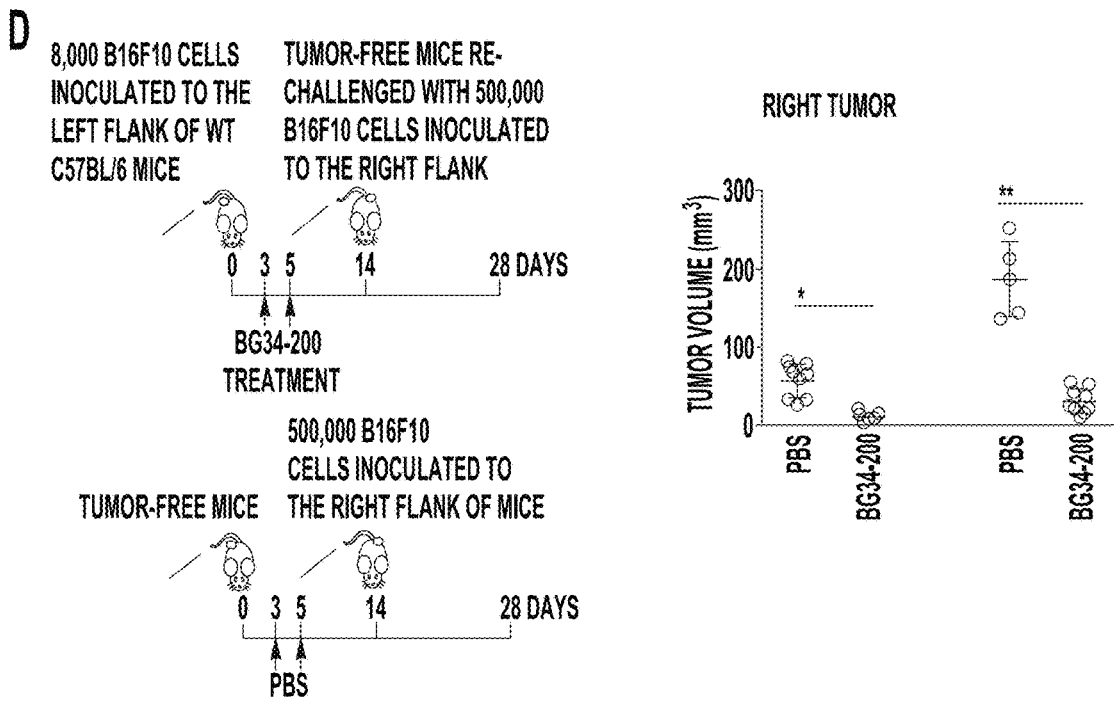

In addition to testing BG34-200 effects in CD11b-KO and CD11c-DTR mouse models, the inventors also treated tumor-bearing nude mice and IFN-γ-KO transgenic mice with BG34-200. The results showed that lymphocytes and IFN-γ were required for the observed BG34-200-induced melanoma regression (FIG. 8A) as compared to WT mice receiving PBS and BG34-200 treatment (FIG. 6C, left). Tumors harvested from nude mice treated with BG34-200 showed a significant increase in mRNA levels of IDO-1, PD-1, iNOS, PDL-1 and TNF-α, while the levels of Arg-1 and TGF-β were significantly decreased (FIG. 8B). In contrast, tumors from BG34-200 treated IFN-γ-KO mice exhibited a significantly decreased mRNA level of CXCR3, IFN-γ, PDL-1, TNF-α and IL-6 while those of CCL3, CCL4, CCR5 and CXCL9 were significantly increased (FIG. 8B).

BG34-200 Treatment Potently Inhibits Osteosarcoma Tumor Growth In Vivo

To test anti-tumor enhancing capacity of BG34-200 beyond melanoma, BG34-200 was administered into Balb/c mice inoculated intratibially with metastatic osteosarcoma cell line, K7M2 (genetic engineered to express luciferase gene Luc2) i.v. to create sarcoma with both primary and lung metastastic lesions. In PBS-treated mice, 75% of the mice developed both primary and metastatic K7M2-Luc2 osteosarcoma tumors. By contrast, while all of the BG34-200-treated mice developed primary tumors on day 28, 80% of these mice showed diminished tumor burden on day 56, at a time when all of the PBS-control mice reached pre-clinical endpoints (FIG. 9).

BG34-200 Treatment of Pancreatic Cancer

BG34-200, in combination with adoptive transfer of tumor draining lymph node (TDLN)-T lymphocytes, was show to significantly improve the survival of mice bearing Aspc-1. The results are shown in FIG. 10. The tumor model used was human AsPC-1 cells, which are metastatic pancreatic adenocarcinoma cells. The tumor cells were inoculated i.p. on day 0. Mice were then treated on day 10. Patient-derived pancreatic tumor draining lymph nodes were cultured in the presence of low dose IL-2 (100 units/mL) and CD3/CD28 activation beads for 14 days. The expanded T cells were adoptively transferred to mice bearing day-10 Aspc-1 at 10$^8$ cells/mouse. Adoptive transfer of T cells in combination with a single dose of BG34-200 was also administered on day-10 tumor-bearing mice. PBS served as negative control. Adoptive transfer of T cells in combination with i.p. single dose of gemcitabine or anti-PD-1 antibody (Nivolumab) served as positive controls. Gemcitabine is reported to reduce tumor-induced myeloid derived suppressor cells (MDSCs) and anti-PD-1 antibody has been discovered to block immune checkpoint signaling pathway. Gemcitabine and nivolumab represent FDA-approved therapeutic agents with different mechanism to reduce tumor-induced immune suppression and enhance T-cell mediated antitumor responses through different mechanism. The adoptive T-cell transfer in combination with BG34-200 showed the highest percentage of survival after 130 days, as compared to all the other control groups.

BG34-200 modulates monocyte-derived CD11b$^+$CD11c$^+$ dendritic cells in tumor site and tumor-draining lymph nodes (TDLNs) to initiate and maintained T cell-mediated antitumor immune responses.

Systemic administration of BG34-200 resulted in significant increase of circulating inflammatory monocytes that gave rise to DCs in tumor sites (FIGS. 11 and 12) and tumor draining lymph nodes (TDLN) (FIG. 13). This associated with T-cell activation (FIG. 14) and resulted in striking regression of melanoma, osteosarcoma and pancreatic tumor (FIGS. 3, 9 and 10). This also resulted in a protective response to secondary tumor challenge in mice (FIG. 14). Mechanistic studies using human monocyte THP-1 cell line revealed that the BG34-200 exposure could promote the monocyte differentiation into dendritic cells (DCs) with significantly upregulated activation markers (CD80, CD86, MHC II and CD11c), increased production of inflammatory cytokine (TNF-α and IL-12) and enhanced phagocytosis (FIG. 15). These results revealed the BG34-modulation of monocytes (innate immunity) for memorable antitumor immune responses (trained antitumor immunity). BG34 in the Mw range of 100 Kda to 300 Kda most effectively promotes the monocyte differentiation into DCs.

Figure 16A:
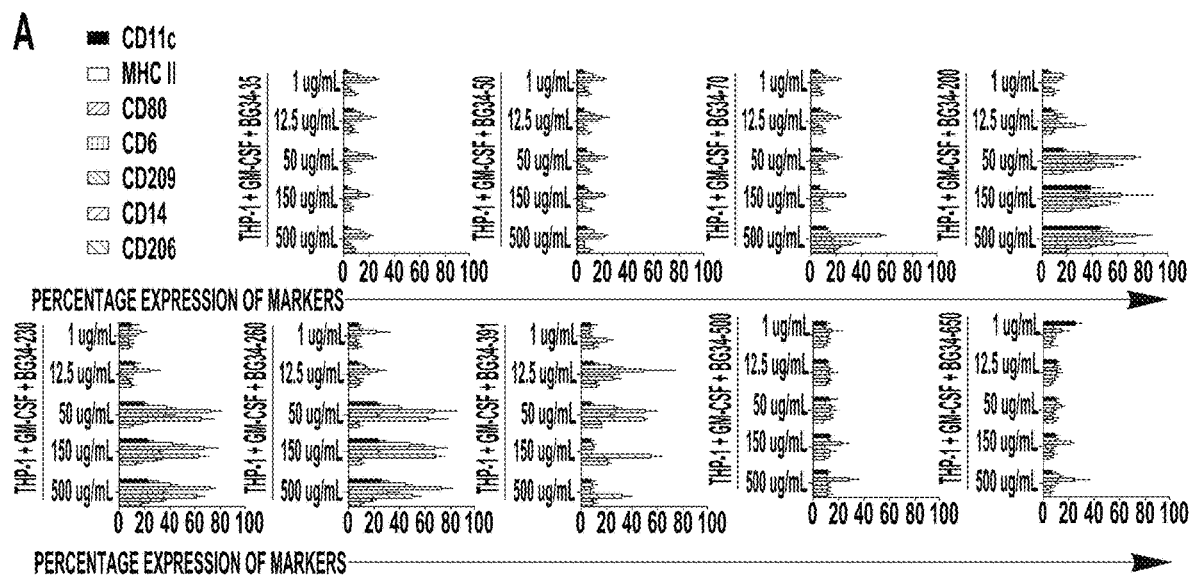
FIGS. 16A-B provides graphs showing the Mw dependence of the BG34-mediated upregulation of CD11c, CD80, CD86, CD209 and MHC II (A) and intracellular production of IL-12 and TNF-α (B). The BG34 in the Mw range of 100-300 Kda most effectively promotes the monocyte differentiation into DCs.
Figure 16B:
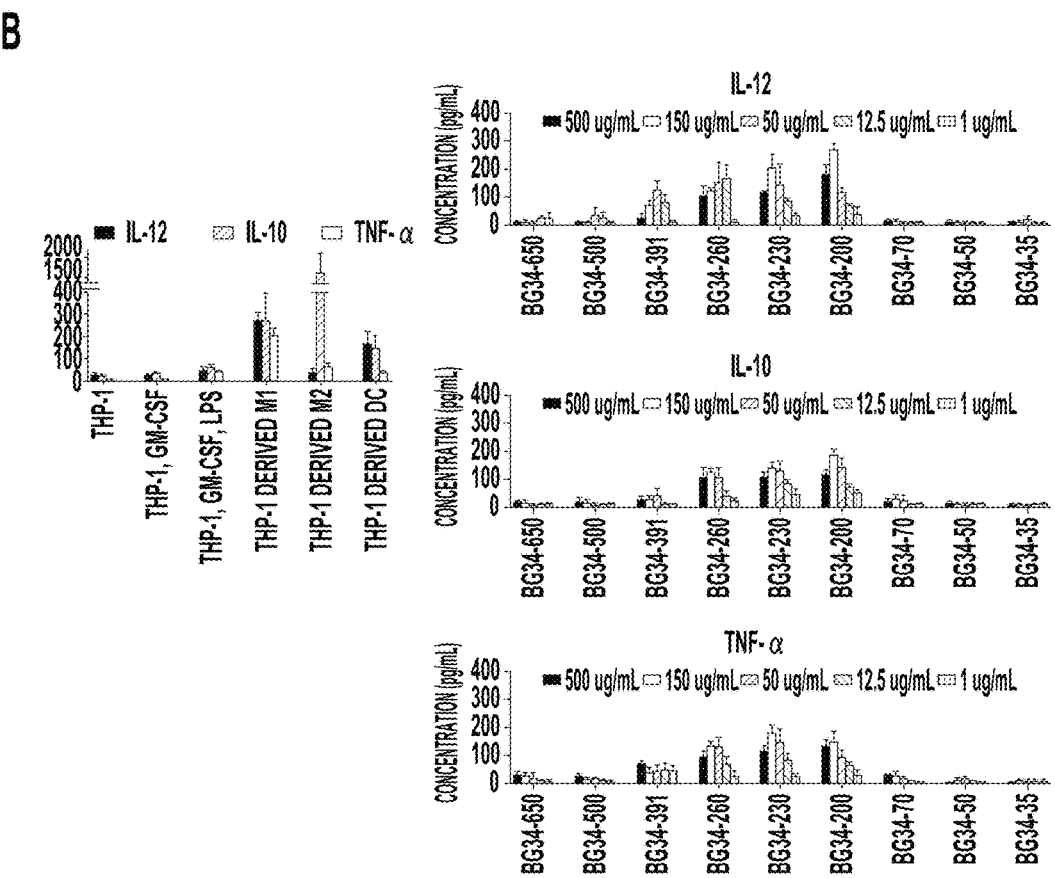

Using the THP-1 cell model, the inventors generated bioanalytical data revealing that the bioactivity of BG34 molecules are significantly affected by Mw. The BG34 molecules in the range 100 Kda-300 Kda can most effectively promote the monocyte differentiation into DCs, thus mediate robust innate and adaptive immune responses against tumor (FIG. 16).

Discussion

Tumor escape can result from the loss of immunogenicity in cancer cells and/or the establishment of an immunosuppressive state within the tumor microenvironment. Quezada, S. A., et al., Immunol Rev, 241(1): p. 104-18 (2011). Therefore, it is critical to devise new therapeutic strategies that are capable of effectively and safely restoring immune-mediated tumor recognition and delivery of effector function. The inventors have demonstrated that an oat-derived β-glucan (BG34) with a specific molecular weight 200 kDa (BG34-200) displays a superior immune stimulating activity at the melanoma tumor sites. Furthermore, the antitumor potency of systemic BG34-200 therapy was demonstrated using both murine model of metastatic melanoma (FIG. 3)

and osteosarcoma in two different genetic strains (FIG. 9). In addition, BG34-200 therapy also augments systemic protective immunity, dramatically reducing distant pulmonary metastases. Therefore, BG34-200 represents a highly potent, non-toxic immune modulator that may be used to overcome cancer-induced immune tolerance.

The systemic administration of BG34-200 has a strong immune modulating impact on the tumor environment, as evidenced by dramatic increases in the levels of inflammatory factors including IFN-γ, TNF-α, CXCL9, CXCL10, IRF1 and PDL-1 in BG34-200-treated tumors (FIGS. 4F and G). The ratios of iNos/Arg1 in the BG34-200-treated tumors within WT mice are also dramatically increased (FIG. 4G), suggesting M1-type activation of macrophages. These changes were associated with significantly increased tumor infiltrations of IFN-γ and Granzyme B producing T cells (FIGS. 4D, E and F). In addition to immune activation in the tumor site, BG34-200 therapy results in systemic mobilization of tumor-reactive T cells, as indicated by lymphocyte activation in TDLN (FIG. 5). These activated T cells contained those that recognize naturally expressed endogenous melanoma antigens, gp100 (FIG. 5).

Knock-out mice studies clearly demonstrate that CD11b$^+$ cells, CD11c$^+$ DCs and T (and possibly NK) cells are involved in the BG34-200-induced immune control of B16F10 (FIGS. 6, 7 and 8). IFN-γ was also critical in the antitumor efficacy of BG34-200 (FIG. 8). Knock-out mice studies demonstrated that CD11b$^+$ myeloid cells, T cells and possibly NK cells are major sources of IFN-γ in tumor sites (FIG. 6D and FIG. 8B). In addition, lack of IFN-γ diminished the BG34-200-induced upregulation of CCL3, CCL4, CCR5, CXCL9, CXCL10, PDL-1, TNF-α, and iNos/Arg1 ratio in tumor site (FIG. 8B). These results emphasize the requirement of CD11b$^+$ myeloid cells for BG34-200-induced activation of tumor-specific effector cells. Although these findings provide mechanistic insights into the therapeutic activity of BG34-200, future studies are necessary to further examine how DC, T or NK cells regulate the antitumor effect of BG34-200 in vivo.

A recent study reported an FDA-approved ferumoxytol nanoparticles that, when co-injected with MMTV-PyMT cancer cells into mice, could suppress tumor growth by introducing M1-type macrophage responses in tumor site. Zanganeh et al., Nat Nanotechnol, 11(11): p. 986-994 (2016). By contrast, this example demonstrates that the systemic administration of BG34-200 to mice bearing established metastatic tumor could result in a robust tumor regression by mediating M1-type macrophage activation and cytotoxic T cell responses in tumor site. This suggests that BG34-200 is much more efficacious than the FDA-approved iron oxide nanoparticles in generating antitumor immunity via modulating macrophages in tumor environment.

On the other hand, glucan-type molecules such as particulate yeast β-glucan have been reported to convert polarized alternatively activated macrophages or immunosuppressive TAM into a classically activated phenotype with potent immunostimulating activity. Nevertheless, particulate yeast glucan exhibits poor water solubility and is administered orally, which limited the bioavailability and clinical efficacy. Chan et al., J Hematol Oncol, 2: p. 25 (2009). Recent studies on small molecular oat-derived beta glucan demonstrate that they have a direct cytotoxic effect on tumor cells by inducing strong expression of caspase-3, -7 and/or -12 in cancer cell lines, resulting in tumor cell apoptosis. Parzonko et al., Int J Biol Macromol, 72: p. 757-63 (2015). However, prior to this work, the in vivo antitumor activity and immune-stimulating effect of oat bran-derived β-glucan containing a well-characterized chemical structure, linear chain (no branches), high purity, free of endotoxin, excellent solubility and specific molecular weight has not been reported. This is the first work to directly demonstrate that BG34-200 is much more efficacious than particulate yeast glucan in generating antitumor immunity in different cancer models tested.

The inventors believe that the efficient uptake and high capacity of BG34-200 to modulate tumor microenvironment contributes to potent macrophage and DC activation after BG34-200 therapy. In vitro BG34-200-treated BM macrophages exhibit significantly enhanced phagocytosis and secretion of TNF-α (FIG. 6B), suggesting a direct effect of BG34-200 on stimulating inflammatory responses of macrophages. Intriguingly, BMDCs exposed to BG34200-treated macrophage conditioned medium were more potent than BMDCs treated directly with BG34-200 in stimulating gp100 specific T cells in vitro (FIGS. 7A and B). This suggests that the BG34-200-treated macrophage conditioned medium contain substances that could potentially enhance DCs antigen processing/presenting function. However, BMDCs cultures with BG34-200 and TNF-α of various concentrations appear not to activate DCs the same way as those with BG34-200 treated BM macrophage condition medium. Indeed, early studies have shown that immune cells including neutrophils, granulocytes and NK cells can interact with macrophage to process and secret bio-active glucan moiety (small fragment of glucan) to participate in immune activation and tumor killing.

In summary, these results demonstrate a profound antitumor effect of systemic administration of BG34-200 in vivo. It is capable of "conditioning" an immune-suppressive/tolergenic tumor environment to result in therapeutic antitumor immunity. However, questions remain with regard to the precise molecular and cellular events triggered by BG34-200. Despite that fact that BG34 functions as a ligand for CR3, these studies suggest that direct monocyte/macrophage activation by BG34-200 may further trigger DCs activation through an as yet undefined signaling pathway. BG34-200-mediated antitumor immunity requires CD11b$^+$ myeloid cells, DCs, and T cells, and driven by IFN-γ. More studies are warranted to further investigate the molecular actions of BG34-200 in vivo and the feasibility of exploiting this novel immune modulator to break tumor-induced immune tolerance in clinical application.

The complete disclosure of all patents, patent applications, and publications, and electronically available materials cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of treating a subject having cancer, consisting of administering a therapeutically effective amount of a pharmaceutical composition consisting of β-(1-3)-(1-4) glucan, a pharmaceutically acceptable carrier, and optionally one or more additives to the subject, wherein the method may further optionally include an additional cancer treatment method selected from chemotherapy, radiation therapy, and adoptive immunotherapy, wherein the β-(1-3)-(1-4) glucan has a molecular weight from 100 to 300 kDa.

2. The method of claim 1, wherein the cancer is metastatic cancer.

3. The method of claim 1, wherein the cancer is melanoma or osteosarcoma.

4. The method of claim 1, wherein the β-(1-3)-(1-4) glucan is oat-derived.

5. The method of claim 1, wherein the β-(1,3)-(1,4) glucan has a molecular weight from 150 to 250 kDa.

6. The method of claim 1, wherein the β-(1,3)-(1,4) glucan has a molecular weight from 190 to 210 kDa.

7. The method of claim 1, wherein the β-(1,3)-(1,4) glucan has a linear chain structure.

8. The method of claim 1, wherein the subject is human.

9. The method of claim 1, wherein the subject is a companion animal.

10. The method of claim 1, wherein the cancer has developed immune tolerance.

11. The method of claim 1, wherein the cancer is further treated with adoptive immunotherapy using T-lymphocytes.

12. A method of immunostimulation in a subject, consisting of administering an effective amount of a pharmaceutical composition consisting of β-(1-3)-(1-4) glucan, a pharmaceutically acceptable carrier, and optionally one or more additives to the subject, wherein the β-(1-3)-(1-4) glucan has a molecular weight from 100 to 300 kDa.

13. The method of claim 12, wherein the subject has cancer.

14. The method of claim 13, wherein the cancer has developed immune tolerance.

15. The method of claim 12, wherein the β-(1,3)-(1,4) glucan has a molecular weight from 190 to 210 kDa.

16. The method of claim 12, wherein the immunostimulation includes macrophage activation.

17. The method of claim 12, wherein the immunostimulation includes T-cell activation.

18. The method of claim 1, wherein the β-(1,3)-(1,4) glucan is administered via a parenteral or topical route.

* * * * *